(12) United States Patent
Serra

(10) Patent No.: US 9,220,767 B2
(45) Date of Patent: Dec. 29, 2015

(54) VACCINE COMPOSITION FOR USE AGAINST INFLUENZA

(75) Inventor: Vincent Serra, Bondoufle (FR)

(73) Assignee: ABIVAX, Paris (FR)

( * ) Notice: Subject to any disclaimer, the term of this patent is extended or adjusted under 35 U.S.C. 154(b) by 956 days.

(21) Appl. No.: 13/123,122

(22) PCT Filed: Oct. 5, 2009

(86) PCT No.: PCT/EP2009/062894
§ 371 (c)(1),
(2), (4) Date: May 26, 2011

(87) PCT Pub. No.: WO2010/040710
PCT Pub. Date: Apr. 15, 2010

(65) Prior Publication Data
US 2011/0229519 A1    Sep. 22, 2011

Related U.S. Application Data

(60) Provisional application No. 61/103,669, filed on Oct. 8, 2008.

(51) Int. Cl.
*A61K 39/145* (2006.01)
*A61P 31/16* (2006.01)
*A61K 39/39* (2006.01)
*A61K 39/12* (2006.01)
*A61K 39/00* (2006.01)

(52) U.S. Cl.
CPC .............. *A61K 39/145* (2013.01); *A61K 39/12* (2013.01); *A61K 39/39* (2013.01); *A61K 2039/55511* (2013.01); *A61K 2039/55555* (2013.01); *A61K 2039/58* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | |
|---|---|---|
| 4,294,854 A | 10/1981 | Durant et al. |
| 5,242,800 A | 9/1993 | Jimenez et al. |
| 5,604,207 A | 2/1997 | DeFrees et al. |
| 5,767,092 A | 6/1998 | Koezuka et al. |
| 5,780,441 A | 7/1998 | Higa et al. |
| 5,785,975 A | 7/1998 | Parikh |
| 5,849,716 A | 12/1998 | Akimoto et al. |
| 5,936,076 A | 8/1999 | Higa et al. |
| 5,958,426 A | 9/1999 | Moreau et al. |
| 6,054,433 A | 4/2000 | Elias et al. |
| 6,071,884 A | 6/2000 | Koezuka et al. |
| 6,417,167 B1 | 7/2002 | Maruyama et al. |
| 6,531,453 B1 | 3/2003 | Taniguchi et al. |
| 6,610,835 B1 | 8/2003 | Liotta et al. |
| 6,635,622 B2 | 10/2003 | Tomiyama et al. |
| 6,747,010 B2 | 6/2004 | Taniguchi et al. |
| 7,273,852 B2 | 9/2007 | Tsuji et al. |
| 7,273,853 B2 | 9/2007 | Or et al. |
| 7,645,873 B2 | 1/2010 | Savage et al. |
| 7,989,423 B2 | 8/2011 | Savage et al. |
| 2002/0115624 A1 | 8/2002 | Behar et al. |
| 2003/0139351 A1 | 7/2003 | Taniguchi et al. |
| 2003/0153514 A1 | 8/2003 | Yagita |
| 2003/0157113 A1 | 8/2003 | Terman |
| 2003/0157135 A1 | 8/2003 | Tsuji et al. |
| 2004/0127429 A1 | 7/2004 | Tsuji |
| 2004/0166554 A1 | 8/2004 | Chamoles |
| 2004/0266726 A1 | 12/2004 | Yagita |
| 2005/0192248 A1 | 9/2005 | Tsuji et al. |
| 2005/0222048 A1 | 10/2005 | Tsuji et al. |
| 2006/0019246 A1 | 1/2006 | Tsuji et al. |
| 2006/0073118 A1 | 4/2006 | Bendelac et al. |
| 2006/0211856 A1 | 9/2006 | Tsuji et al. |
| 2006/0264382 A1 | 11/2006 | Savage et al. |
| 2008/0095787 A1 | 4/2008 | Teyton |
| 2008/0279894 A1 | 11/2008 | Teyton et al. |
| 2009/0047299 A1 | 2/2009 | Savage et al. |
| 2010/0137231 A1 | 6/2010 | Savage et al. |
| 2011/0229519 A1* | 9/2011 | Serra .................. 424/210.1 |
| 2012/0028915 A1 | 2/2012 | Savage et al. |
| 2012/0270815 A1 | 10/2012 | Savage et al. |

FOREIGN PATENT DOCUMENTS

| | | |
|---|---|---|
| EP | 0988860 | 3/2000 |
| EP | 1016409 | 7/2000 |
| WO | WO 99/33475 | 7/1999 |
| WO | WO 03/009812 | 2/2003 |
| WO | WO 03/018039 | 3/2003 |
| WO | WO 03/105769 | 12/2003 |
| WO | WO 2004/094444 | 11/2004 |
| WO | WO 2005/000348 | 1/2005 |
| WO | WO 2005/102049 | 11/2005 |
| WO | WO 2006/026389 | 3/2006 |
| WO | WO 2006/029010 | 3/2006 |

(Continued)

OTHER PUBLICATIONS

De Jong et al. (Nature Medicine. 2006;; 12 (10): 1203-1207).*
Tumpey et al. (Science. 2005; 310: 77-80).*
Rose et al. (Expert Opinion in Biological Therapeutics. 2006; 6 (3): 301-310).*
Galli et al. (PNAS. 2007; 104 (10): 3984-3989).*
PCT/EP2009/062894 International Search Report (Dec. 23, 2009).
Liu et al., "A Modified alpha-Galactosyl Ceramide for Staining and Stimulating Natural Killer T Cells," Journal of Immunological Methods, vol. 312, pp. 34-39 (2006).

(Continued)

*Primary Examiner* — Shanon A Foley
(74) *Attorney, Agent, or Firm* — Merchant & Gould P.C.

(57) ABSTRACT

The present invention relates to a vaccine composition comprising: —at least one prophylactically active agent against influenza, and —at least one adjuvant, said adjuvant being a derivative of a galactosylceramide, for use in the treatment of influenza.

10 Claims, 20 Drawing Sheets

(56) References Cited

FOREIGN PATENT DOCUMENTS

| WO | WO 2006/083671 | 8/2006 |
|---|---|---|
| WO | WO 2007/007946 | 1/2007 |
| WO | WO 2007/050668 | 5/2007 |
| WO | WO 2007/118234 | 10/2007 |
| WO | WO 2007/126163 | 11/2007 |
| WO | WO 2008/005824 | 1/2008 |
| WO | WO 2008/080926 | 7/2008 |
| WO | WO 2008/082156 | 7/2008 |
| WO | WO 2010/040710 | 4/2010 |

OTHER PUBLICATIONS

Kamijuku et al., "Mechanism of NKT Cell Activation by Intranasal Coadministration of alpha-Galactosylceramide, which can Induce Cross-Protection Against Influenza Viruses," Nature, vol. 1(3), pp. 208-218 (May 2008).

Kopecky-Bromberg et al., "Alpha-C-Galactosylceramide as an Adjuvant for a Live Attenuated Influenza Virus Vaccine," Vaccine, vol. 27, pp. 3766-3774 (2009).

Hilleman, M.R., "Realities and enigmas of human viral influenza: pathogenesis, epidemiology and control," Vaccine (2002) 20: 3068-3087.

Ando et al., "Solid-phase capture-release strategy applied to oligosaccharide synthesis on a soluble polymer support," Agnew. Chem. Int. Ed. (2001) 40:4725-4728.

Beaudoin, L. et al., "NKT cells inhibit the onset of diabetes by impairing the development of pathogenic T cells specific for pancreatic beta cells," Immunity (2002) 17:725-736.

Bendelac et al., "Increased interleukin 4 and immunoglobulin E production in transgenic mice overexpressing NK1 T cells," J. Exp. Med. (1996) 184: 1285-1293.

Bendelac, A. et al., "Autoreactivity by design: innate B and T lymphocytes," Natur. Rev. Immunol. (2001) 1:177-186.

Bendelac, A. et al., "The biology of NKT cells," Ann. Rev. Immunol. (2007) 25:297-336.

Bendelac, A., "Nondeletional pathways for the development of autoreactive thymocytes," Nat. Immunol. (2004) 5:557-558.

Benlagha, K. et al., "In vivo identification of glycolipid antigen-specific T cells using fluorescent CD1d tetramers," J. Exp. Med. (2000) 191:1895-1903.

Brigl et al., "Mechanism of CD1d-restricted natural killer T cell activation during microbial infection," Nat. Immunol. (2003) 4: 1230-1237.

Brigl et al., "T cell function and antigen presentation," Annu. Rev. Immunol. (2004) 22: 817-890.

Brossay, L. et al., "Cutting edge: structural requirements for galactosylceramide recognition by CD1-restricted NK T cells," J. Immunol. (1998) 161(10):5124-5128.

Brutkiewicz et al., "CD1d-mediated antigen presentation to natural killer T (NKT) cells," Critical Reviews in Immunology (2003) 23: 403-419.

Brutkiewicz et al., "Natural killer T (NKT) cells and their role in antitumor immunity," Critical Reviews in Oncology/Hematology (2002) 41: 287-298.

Cantu et al., "The paradox of immune molecular recognition of alpha-galactosylceramide; low affinity, low specificity for CD1d, high affinity for alpha beta TCRs," J. Immunol. (2003) 170: 4673-4682.

Cochlovius et al., Modern Drug Discovery (2003), 33-38.

Corey et al., "A new method for the synthesis of organic nitro compounds," J. Am. Chem. Soc. (1984) 106:3682-3683.

Daoudi, J-M. et al., "New bicyclam-galcer analogue conjugates: synthesis and in vitro anti-HIV activity," Biorg. Med. Chem. Lett. (2004) 14:495-498.

Dascher, C.C. et al., "CD1 Antigen Presentation (2003) 10:164-182. and Infectious Disease," Contributions to Microbiology (2003) 10:164-182.

Davis, N.J. et al., "Chemical Synthesis of Disaccharides Which are Partial Structures of the Glycosaminoglycan Heparan Sulfate," J. Chem. Soc. (1994) 1:359-368.

De Libero, G. et al., "Self glycosphingolipids: new antigens recognized by autoreactive T lymphocytes," News Physiol. Sci. (2003) 18:71-76.

European Office Action for Application No. 03816701.1 dated Nov. 29, 2007.

European Office Action for Application No. 05810863.0 dated Apr. 2, 2008.

Feldman et al., Transplant Proc. (1998) 30:4126-4127.

Fischer, K. et al., "Mycobacterial phosphatidylinositol mannoside is a natural antigen for CD1d-restricted T cells," Proc. Natl. Acad. Sci. USA (2004) 101:10685-10690.

Fuji et al., "Antitumor effect of α-galactosylceramide (KRN7000) on spontaneous hepatic metastases requires endogenous interleukin 12 in the liver," Clinical Cancer Research (2000) vol. 6, No. 8, pp. 3380-3387.

Fujii et al., "Activation of natural killer T cells by alpha-galactosylceramide rapidly induces the full maturation of dendritic cells in vivo and thereby acts as an adjuvant for combined CD4 and CD8 T cell immunity to a coadministered protein," J. Exp. Med. (2003) 198:267-279.

Garrity, G.M. et al., Taxonomic Outline of the Procaryotic Genera, Bergey's Manual of Systematic Bacteriology, 2nd Edition (Apr. 2001).

Godfrey, D.I. et al., "Going both ways: immune regulation via CD1d-dependent NKT cells," J. Clin. Invest. (2004) 114(10):1379-1388.

Godfrey, D.I. et al., "The elusive NKT cell antigen—is the search over?" Science (2004) 306:1687-1688.

Goff, R.D. et al., "Effects of lipid chain lengths in alpha-galactosylceramides on cytokine release by natural killer T cells," J. Am. Chem. Soc. (2004) 126:13602-13603.

Goodman & Gilman's The Pharmacological Basis of Therapeutics, Tenth Edition, Hardman and Limbird, editors, The McGraw-Hill Companies, Inc., New York, (2001) 54-56.

Gui, M. et al., "TCR beta chain influences but does not solely control autoreactivity of V alpha 14J28IT cells," J. Immunol. (2001) 167(11):6239-6246.

Gumperz, J.E. et al., "Functional distinct subsets of CD1d-restricted natural killer T cells revealed by CD1d tetramer staining," J. Exp. Med. (2002) 195(5):625-636.

Gumperz, J.E. et al., "Murine CD1d-restricted T cell recognition of cellular lipids," Immunity (2000) 12:211-221.

Gupta, R.K. et al., "Adjuvants—a balance between toxicity and adjuvanticity," Vaccine (1993) 11(3):293-306.

Hashimoto, S. et al., "Glycosylation Using Glucopyranosyl Fluorides and Silicon-Based Catalysts, Solvent Dependency of the Stereoselection," Tetrahedron Letters (1984) 25:13:1379-1382.

Hayashi, M. et al., "Simple Synthesis of Glycosyl Fluorides," Chem. Letters (1984) 1747-1750.

Hermans, I.F. et al., "NKT cells enhance CD4+ and CD8+ T cell responses to soluble antigen in vivo through direct interaction with dendritic cells," J. Immunol. (2003) 171:5140-5147.

Honey, K. et al., "Thymocyte expression of cathepsin L is essential for NKT cell development," Nat. Immunol. (2002) 3:1069-1074.

Iida, N. et al., "A sulfated glucosylceramide from rat kidney," J. Biol. Chem. (1989) 264(10):5974-5980.

Islam, I. et al., "Synthesis and antiviral activity of (2-((4-(3-((1-methylethyl)amino)-2-pyridy1)-1-piperazinyl)carbony)-1H-indo 1-5-yl) (BHAP) acylspingosine HIV reverse transcriptase inhibitors," Biorg. Chem, (1995) 23(4):499-511.

Ismail, N. et al., "Overproduction of TNF-alpha b CD8+ type 1 cells and down-regulation of IFN-γ production by CD4+ Th1 cells contribute to toxic shock-like syndrome in an animal model of fatal monocytotropic ehrlichiosis," J. Immunol. (2004) 172:1786-1800.

Karadimitris, A. et al., "Human CD1d-glycolipid tetramers generated by in vitro oxidative refolding chromatography," Proc. Natl. Acad. Sci. USA (2001) 98(6):3294-3298.

Kawano, T. et al., "CD1d-restricted and TCR-mediated activation of Vα14 NKT cells by glycosylceramides," Science (1997) 278:1626-1629.

Khan, M. et al., "Syntheses and Antiinflammatory Activity of Some 6-aryl-2,3,4,5-tetrahydro-3-pyridazinones," Indian J. Chem. (2000) 39B:614-619.

(56) References Cited

OTHER PUBLICATIONS

Kinjo, Y. et al., "Recognition of bacterial glycosphingolipids by natural killer T cells," *Nature* (2005) 434:520-525.
Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," *J. Exp. Med.* (1999) 189:1121-1127.
Ko et al. "α-Galactosylceramide Can Act As a Nasal Vaccine Adjuvant Inducing Protective Immune Responses against Viral Infection and Tumor." *Journal of Immunology.* vol. 175. No. 5.2005. pp. 3309-3317.
Kronenberg, M., "Toward an understanding of NKT cell biology: progress and paradoxes," *Ann. Rev. Immunol* (2005) 23:877-900.
Laurence et al., *Nature Immunol* (2007), 9:903-905.
Lee, P.T. et al., "Testing the NKT cell hypothesis on human IDDM pathogenesis," *J. Clin. Invest.* (2002) 110(6):793-800.
Lei et al., *Bioorganic & Medicinal Chemistry* (1998) 6:1337-46.
Liu et al., "A modified alpha-galactosyl ceramide for staining and stimulating natural killer T cells." *Journal of Immunological Methods* (2006) pp. 34-39.
Long et al., "Synthesis and evaluation of stimulatory properties of *Sphingomonadaceae* glycolipds," *Nature Chemical Biology* (2007) 9: 559-564. XP002542183.
Matsuda, J.L. et al., "Tracking the response of natural killer T cells to a glycolipid antigen using CD1d tetramers," *J. Exp. Med.* (2000) 192(5):741-753.
Mattner, J. et al., "Exogenous and endogenous glycolipid antigens activate NKT cells during microbial infections," *Nature* (2005) 434:525-529.
Miyamoto, K. et al., "A Synthetic Glycolipid Prevents Autoimmune Encephalomyelitis by Inducing TH2 Bias of Natural Killer T Cells," *Nature* (2001) 413:531-534.
Morita, M. et al., "Structure-Activity Relationship of α-Galactosylceramides Against B16-Bearing Mice," *J. Med. Chem.* (1995) 38:2176-2187.
Nakagawa, R. et al., "Mechanisms of the Antimetastatic Effect in the Liver and of the Hepatocyte Injury Induced by α-Galactosylceramide in Mice," *J. Immun.* (2001) 166:11:6578-6584.
Pal, E. et al., "Co stimulation-Dependent Modulation of Experimental Autoimmune Encephalomyelitis by Ligand Stimulation of Vα14 NK T Cells," *J. Immunol.* (2001) 166:662-668.
Park, S.H. et al., "CD1-restricted T-cell responses and microbial infection," *Nature* (2000) 406:788-792.
Park, S.H. et al., "The Mouse CD1d-restricted Repetoire is Dominated by a Few Autoreactive T cell Receptor Families," *J. Exp. Med.* (2001) 8:893-904.
Park, S.-H. et al., "Tissue-specific recognition of mouse CD1 molecules," *J. Immunol.* (1998) 160:3128-3134.
Petrovsky, N. et al., "Vaccine adjuvants: current state and future trends," *Immunol. Cell Biol.* (2004) 82:488-496.
Prigozy, T.I. et al., "Glycolipid antigen processing for presentation by CD1d molecules," *Science* (2001) 291:664-667.
Rock, K.L. et al., "Natural endogenous adjuvants," *Springer Semin Immunopathol.* (2005) 26:231-246.
Sakai, T. et al., "Effects of α- and β-Galactosylated C2-Ceramides on the Immune System," *J. Med. Chem.* (1998) 41:650-652.
Sidobre, S. et al., "CD1d tetramers: a powerful tool for the analysis of glycolipid reactive T cells," *J. Immunol. Methods* (2002) 268:107-121.
Silk et al. "Utilizing the adjuvant properties of CD1d-dependent NK T cells in T cell-mediated immunotherapy." *Journal of Clinical Investigation.* vol. 114. No. 12. 2004. pp. 1810-1811.
Sinay, P. et al., *Bioorganic and Medicinal Chemistry* (1998) 6: 1337-46.
Singh et al., "The natural killer T Cell ligand Alpha-Galactosylceramide protects mice against EAE by an IL-4-and IL-10- dependent mechanism," *FASEB J., Fed. Of Amer. Soc. For Exp. Bio* (2002) 16: A1043.

Singh, P.P. et al., "The Synthesis of 2,3,4,6,7-Penta-O-Methyl-D-glycero-L-manno-Heptose and 2,4,6,7-Tetra-O-Methyl-D-glycero-L-manno-Heptose," *Carbohydrate Res.* (1970) 12:261-266.
Smyth, M.J. et al., "NKT cells—conductors of tumor immunity?" *Curr. Opin. Immunol.* (2002) 14(2):165-171.
Smyth, M.J. et al., "NKT cells and tumor immunity—a double-edged sword," *Nature Immunology* (2001) 1:459-460.
Stanic A.K. et al., "Defective presentation of the CD1d1-restricted natural Val4Ja18 NKT lymphocyte antigen caused by Beta-D-glucosylceramide synthase deficiency," *Proc. Natl. Acad. Sci. USA* (2003) 100:1849-1854.
Supplemental European Search Report for EP Application No. 07760333.0 mailed Sep. 3, 2010.
Supplementary European Search Report for EP Application No. 03816701.1 mailed Sep. 17, 2007.
Takikawa et al., "Diastereoselective Epoxidation of the Double Bond at C-4 of Sphingosines to Provide Phytosphingosine Relatives such as α-Galactosylceramide KRN7000," *Tetrahedron* (1998) 54:3141-3150.
The Merck Manual, 16th Edition (1999): pp. 339-342 and 1488-1490.
United States Office Action for U.S. Appl. No. 10/550,165 mailed Oct. 27, 2008.
United States Office Action for U.S. Appl. No. 10/550,165 mailed Jan. 9, 2008.
United States Office Action for U.S. Appl. No. 10/550,165 mailed Jul. 20, 2007.
United States Office Action for U.S. Appl. No. 10/550,165 mailed Apr. 12, 2007.
United States Office Action for U.S. Appl. No. 11/218,906 mailed Nov. 10, 2008.
United States Office Action for U.S. Appl. No. 11/771,128 mailed Oct. 29, 2008.
United States Office Action for U.S. Appl. No. 12/296,169 mailed May 11, 2011.
United States Office Action for U.S. Appl. No. 12/625,048 mailed Sep. 29, 2010.
United States Office Action for U.S. Appl. No. 13/196,631 mailed Jul. 17, 2012.
Van Der Vliet, H.J.J. et al., "Effects of α-galactosylceramide (KRN7000), interleukin-12 and interleukin-7 on phenotype and cytokine profile of human Vα24+ Vβ11+T cells," *Immunology* (1999) 98:557-563.
Van Kaer, L., "Alpha-galactosylceramide therapy for autoimmune diseases: prospects and obstacles," *Nat. Rev. Immunol.* (2005) 5:31-42.
Vandommelen, S.L.H. et al., "Activation of natural killer (NK) T cells during murine cytomegalovirus infection enhances the antiviral response mediated by NK cells," *J. Virology* (2003) 77(3):1877-1884.
Vaultier, M. et al., "Reduction d'azides en amines primaires par une methode generale utilisant la reaction de staudinger," *Tetrahedron Letters* (1983) 24:763 (Not in English).
Wang, B. et al., "CD1-Restricted NK T Cells Protect Nonobese Diabetic Mice from Developing Diabetes," *J. Exp. Med.* (2001) 194:313-319.
Wang, F. et al., "Tuning of Binding Selectivity: Metal Control of Organic Guest Binding and Allosteric Perturbation of Fluorescent Metal Sensor," *J. Org. Chem.* (1999) 64:8922-8928.
Weber, G. et al., "Synthesis and Spectral Properties of a Hydrophobic Fluorescent Probe: 6-Propionyl-2-(dimethylamino) naphthalene," *Biochem,* (1979) 18:14:3075-3078.
Winau, F. et al., "Saposin C is required for lipid presentation by human CD1b," *Nat. Immunol.* (2004) 5:169-174.
Wu et al., "Bacterial glycolipids and analogs as antigen for CD1d-restricted NKT cells," *PNAS* (2005) 102(5):1351-1356.
Wu, D.Y. et al., "Cross-presentation of disialoganglioside GD3 to natural killer T cells," *J. Exp. Med.* (2003) 198:173-181.
Xia, C. et al., "Thio-isoglobotrihexosylceramide, an Agonist for activating invariant natural killer T cells," *Org. Lett.* (2006) 8(24):5493-5496.
Yamaguchi et al., *Oncology Research, Pergamon Press,* "Enhancing Effects of (2S, 3S, 4R)-1-0-0 Alpha-D-Galactopyranosyl)-2-(N-Hexacosanoylamino)-1, 3, 4-Octadecanetriol (KRN7000) on Antigen-Presenting Function of Antigen-Presenting Cells and

(56) References Cited

OTHER PUBLICATIONS

Antimetastatic Activity of KRN7000-Pretreated Antigen-Presenting Cells.", Jan. 1996, vol. 8, No. 10-11, pp. 399-407.
Yu, K.O.A. et al., "Modulation of CD1d-restricted NKT cell responses by using N-acyl variants of alpha-galactosylceramides," *Proc. Natl. Acad. Sci. USA* (2005) 102(9):3383-3388.
Zajonc, D.M. et al., "Structural basis for CD1d presentation of a sulfatide derived from myelin and its implications for autoimmunity," *J. Exp. Med.* (2005) 202(11):1517-1526.
Zajonc, D.M. et al., "Structure and function of a potent agonist for the semi-invariant natural killer T cell receptor," *Nat. Immunol.* (2005) 6:810-818.
Zhou et al., "Synthesis and NKT cell stimulating properties of fluorophore-and biotin-appended 6'-amino-6'deoxy-galactosylceramides," *Org. Lett.* (2002) 4(8):1267-1270. XP003008968.
Zhou, D. et al., "Editing of CD1d-bound lipid antigens by endosomal lipid transfer proteins," *Science* (2004) 303:523-527.
Zhou, D. et al., "Lysosomal glycosphingolipid recognition by NKT cells," *Science* (2004) 306:1786-1789.
Zhou, D., "The immunological function of iGb3," *Curr. Prot. Pept. Sci.* (2006) 7:325-333.
International Search Report for Application No. PCT/US2005/031407.
Written Opinion for Application No. PCT/US2005/031407.
International Search Report for International Application No. PCT/US2007/072451.
Written Opinion for International Application No. PCT/US2007/072451.
International Search Report for International Application No. PCT/US06/002781.
Written Opinion for International Application No. PCT/US06/002781.
International Search Report for International Application No. PCT/US07/66250.
Written Opinion for International Application No. PCT/US07/66250.
International Search Report for International Application No. PCT/US03/08530.
Written Opinion for International Application No. PCT/US03/08530.

\* cited by examiner

H5N1 challenge, Fluarix 1/30.000, PBS96 100ng

- Mock
- Flu Vaccine
- PBS96
- PBS96+Vaccine
- Control

FIG.17

VACCINE COMPOSITION FOR USE AGAINST INFLUENZA

CROSS-REFERENCE TO RELATED APPLICATIONS

This application is a National Stage Application of International Application No. PCT/EP2009/062894, filed 5 Oct. 2009, which claims benefit of U.S. Provisional Application Ser. No. 61/103,669, filed 8 Oct. 2008 and which claims applications are incorporated herein by reference. To the extent appropriate, a claim of priority is made to each of the above disclosed application The present invention relates to a vaccine composition, in particular for use against influenza.

Human and avian influenza are widespread pandemias with high levels of mortality and morbidity each season. Among influenza viruses, which are enveloped RNA viruses which belong to the family of Orthomyxoviridae, the principal cause of influenza is the influenza A virus. Influenza A virus can be further differentiated into subtypes by the antigenic properties of its surface proteins: hemagglutinin (H) and neuraminidase (N). Fifteen H and nine N subtypes have been identified until now. Although many combinations of these subtypes have been found in animals, only H1, H2, H3, N1 and N2 have established stable lineages in the human population since 1918.

Influenza A has a high natural mutation rate and changes its antigenic characteristics frequently, either by gradual antigenic drift over time (that is to say by random point mutations inserted by the virus polymerase, translating into changes in the amino acid sequence of the respective proteins), or by sudden recombination with another virus subtype, known as antigenic shift (when an host is simultaneously infected with two different strains of influenza virus).

The main strategy used to fight the disease is vaccination with either inactivated or live attenuated vaccines.

Various vaccines have been developed against influenza such as the seasonal influenza vaccines Fluzone®, Vaxigrip®, Mutagrip® and Imovax Gripe® commercialized by Sanofi-Pasteur, Fluarix®, Gripovax®, and FluLaval® commercialized by GlaxoSmithKline, FluMist® commercialized by MedImmune, Afluria® commercialized by CSL Biotechnologies or Begrivac®, Fluad®, Fluvirin® and Agrippal® commercialized by Novartis. Influenza vaccines also include pandemic influenza vaccines such as Celvapan® (Baxter), Daronrix®, Pandemrix® and Prepandrix® (GlaxoSmithKline Biologicals), Focetria® and Optaflu® (Novartis Vaccines and Diagnostics), IDflu® and Intanza® (Sanofi Pasteur). Nevertheless, available vaccines are active for short periods of time and only for specified strain types (hemagglutinins). Emergence of resistant viral variants and adverse effect created a need for improved prevention of influenza virus infections, in particular of simultaneous prevention of distinct influenza virus strains infections.

Surprisingly, the inventors have found that the use of a derivative of galactosylceramides as an adjuvant in an influenza vaccine increased the potency of the vaccine composition. Specifically, they showed that such compounds increased the isotype switching (increased production of IgG2a and IgG2b) and unexpectedly induced the activation of cytotoxic T lymphocytes against the influenza epitope, in particular a Th1 activation, whereas current flu vaccines mainly increase the IgG production.

Additionally, the inventors surprisingly showed that the use of a derivative of galactosylceramides as an adjuvant in an influenza vaccine induced a cross protection, i.e. they increased the potency of the vaccine composition towards an infecting strain different from the strain used for manufacturing the influenza vaccine.

The present invention thus relates to a vaccine composition comprising:
  at least one prophylactically active agent against influenza, said prophylactically active agent against influenza optionally containing an adjuvant, and
  at least one adjuvant, said adjuvant being a derivative of a galactosylceramide.

In the context of the invention, a "vaccine composition" or "vaccine" refers to a composition which, when administered to a subject, induces cellular and/or humoral immune responses.

"Subject" refers herein to an animal, such as a vertebrate or a mammal, preferably a non-human or human mammal. Examples of vertebrates include birds and poultry, in particular chicken. Examples of non-human mammals include rodents, horses, swine and primates. Most preferably, a subject is human.

In the context of the invention, "influenza" or "flu" refers to an infectious disease of birds and mammals caused by RNA viruses of the family Orthomyxoviridae, named influenza virus. In humans, common symptoms of the disease are chills and fever, sore throat, muscle pains, severe headache, coughing, weakness and general discomfort. In more serious cases, influenza causes pneumonia, which can be fatal, particularly in young children and the elderly. Influenza may be transmitted from infected mammals through the air by coughs or sneezes, creating aerosols containing the virus, and from infected birds through their droppings. Influenza may also be transmitted by saliva, nasal secretions, feces and blood. Infections may also occur through contact with these body fluids or with contaminated surfaces.

In the context of the invention, an "influenza virus" refers to the causative agent of flu. It is an enveloped RNA virus with a segmented genome consisting of eight single-stranded negative RNA segments, and belongs to the family of Orthomyxoviridae. Influenza viruses according to the invention encompass the three subtypes Influenza A, Influenza B and Influenza C viruses. These subtypes are based on antigenic differences in two of the structural proteins of the virus—the matrix protein M2 and the nucleoprotein. Preferably the influenza virus according to the invention is an Influenza A virus. More preferably, the influenza virus is selected from the group consisting of the strains H1N1, H1N2, H2N2, H3N1, H3N2, H5N1 and H7N7 strains. More particularly, it is well-known from the one skilled in the art, that influenza may be seasonal or pandemic. Seasonal influenza is typically due to a strain defined and recommended by the Word Health Organization. Currently (in 2009), circulating influenza strains causing seasonal influenza are in particular H1N1, H3N2 and B influenza strains. In the past, H2N2 influenza strain was also responsible for seasonal influenza. Until 2008, pandemic influenza was for example due to H1N1 or H7N7 influenza strains.

A "prophylactically active agent" as used herein refers to any compound of organism liable to induce an immune response against an infection by an influenza virus. Examples of prophylactically active agents which may be suitable against influenza include polypeptide, polynucleotide, carbohydrate moiety, glycoprotein, whole influenza virus, split influenza virus. Preferably, the at least one prophylactically active agent against influenza according to the invention is selected from the group consisting of a live non-attenuated influenza virus; a live attenuated influenza virus; a killed or inactivated influenza virus; an influenza virus antigen such as a subunit of an influenza virus, a recombinant polypeptide or protein from an influenza virus; a cDNA from an influenza virus or a recombinant influenza virus.

Preferably, the at least one prophylactically active agent against influenza according to the invention comprises at least one Influenza A virus strain and at least one Influenza B virus strain, and optionally another Influenza A virus strain or one Influenza C virus strain.

As used herein, a "live non-attenuated influenza virus" refers to a living enveloped RNA virus with a segmented genome consisting of eight single-stranded negative RNA segments, and belonging to the family of Orthomyxoviridae.

As used herein, a "live attenuated influenza virus" refers to living influenza virus strain displaying a naturally weak virulence. Live attenuated influenza viruses include strains of influenza that are cold-adapted and temperature-sensitive. Methods to obtain live attenuated viruses are well-known from those skilled in the art and include serial passages in hen eggs until obtaining mutants that have lost their pathogenic potential (Hilleman (2002) *Vaccine* 20:3068-3087).

As used herein, a "killed influenza virus" or "inactivated influenza virus" refers to killed influenza viruses obtained by known methods, the most common of which is to grow the virus in fertilized hen eggs, to purify it and to inactivate it, for example, by treatment with detergent.

As used herein, a "subunit of an influenza virus" refers to a nucleic acid, a polypeptide, a protein from said influenza virus or a mixture thereof. In particular, a subunit of an influenza virus is a protein of said influenza virus selected from the group consisting of hemagglutinin, neuraminidase, nucleoprotein, M1, M2, NS1, NS2(NEP), PA, PB1, PB1-F2 and PB2. Preferably, according to the invention, the subunit of an influenza virus is hemagglutinin and/or neuraminidase.

Preferably, the influenza virus according to the invention originates from a host which is an animal, in particular a mammal or a bird. More preferably, the host of the influenza virus is selected from the group consisting of a human, a horse and a bird.

In the context of the invention, an "adjuvant" refers to a substance that increase or modify the immunogenic potency of the prophylactically active agent.

As used herein, the expression "derivative of a galactosylceramide" designates galactosylceramides, such as α-galactosylceramide, and more particularly derivatives thereof.

Preferably, the derivative of a galactosylceramide according to the invention is an NKT cell activating derivative of galactosylceramide. As used herein, an "NKT cell activating derivative of galactosylceramide" refers to a derivative of a galactosylceramide that leads (i) to secretion by NKT cells of Th1 and Th2 cytokines, such as IFN-γ, IL-4, IL-2, IL-10, IL-13, GM-CSF or TNF-α, or combinations of these cytokines, upon contact with CD1d-presented stimulatory antigens, or (ii) to up-regulated expression of cell-surface markers for activated T-cells such as CD69, or (iii) to B-cells activation or (iv) to down regulation of the T cells receptor (TCR) at the surface of NKT cells.

Preferably, the adjuvant according to the invention is a compound having the following formula (V):

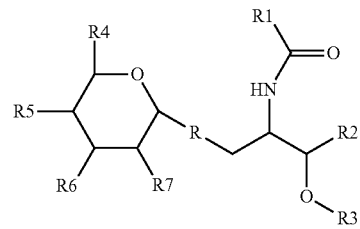

wherein:
R is an oxygen or a sulphur atom or —CH$_2$—;

$R_1$ is a saturated or unsaturated, optionally aromatic, linear or branched hydrocarbon chain such as an alkyl, aryl, aralkyl, alkenyl, or aralkenyl chain, comprising from 1 to 150 carbon atoms, optionally comprising one or more heteroatoms or groups preferably selected among O, N, S or a carbonyl group, and optionally substituted by one or more hydroxyl or cyclopropyl groups;

$R_2$ is a saturated or unsaturated, optionally aromatic, linear or branched hydrocarbon chain such as an alkyl, aryl, aralkyl, alkenyl or aralkenyl chain, comprising from 1 to 150 carbon atoms, optionally comprising one or more heteroatoms or groups preferably selected among O, N, S or a carbonyl group, and optionally substituted by one or more hydroxyl groups or by a saturated or unsaturated hydrocarbon chain comprising from 1 to 20 carbon atoms;

$R_3$ is an hydrogen atom or a saturated or unsaturated, optionally aromatic, linear or branched hydrocarbon chain such as an alkyl, aryl, aralkyl, alkenyl or aralkenyl chain, comprising from 1 to 120 carbon atoms;

$R_4$, $R_5$, $R_6$ and $R_7$, identical or different, represent (i) an hydroxyl group or (ii) a saturated or unsaturated, optionally aromatic, linear or branched hydrocarbon chain such as an alkyl, aryl, aralkyl, alkenyl or aralkenyl chain, comprising from 1 to 100 carbon atoms, optionally comprising one or more heteroatoms or groups preferably selected among O, N, S or a carbonyl group; or (iii) an amino, sulphate, phosphate or carboxyl group, or (iv) a chain of 1 to 4 hexoses, optionally substituted by one or more groups selected from an amino, a sulphate, a phosphate and a carboxyl group, the hexoses being linked one to the other by an oxygen or a sulphur atom or —CH$_2$—.

More preferably, the adjuvant according to the invention is a compound having the following formula (VI):

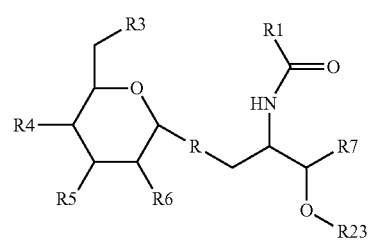

wherein
$R_1$ is (i) —(CH$_2$)$_X$CH$_3$ wherein X is an integer selected from 1 to 100; or
(ii) —(CH$_2$)$_X$CH=CH(CH$_2$)$_Y$CH$_3$ or —(CH$_2$)$_X$CH=CH(CH$_2$)$_Y$CH=CH(CH$_2$)$_Z$CH$_3$ wherein X, Y and Z are integers independently selected from 1 to 14; or (iii) a group represented by formula (A)

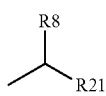

wherein $R_8$ is H or OH and $R_{21}$ is a $C_1$-$C_{30}$ alkyl, wherein the $C_1$-$C_{30}$ alkyl is saturated or unsaturated or comprises one or more cyclopropyl groups;

$R_2$ is a linear or branched $C_3$-$C_{100}$ alkyl;

$R_3$, $R_4$ and $R_6$, identical or different, represent
(i) —O—$R_{22}$
wherein $R_{22}$ is hydrogen, $C_1$-$C_6$ alkyl, $C_6$-$C_{12}$ aralkyl or $C_1$-$C_6$ acyl; or
(ii) —$NR_{24}$—CO—$CH_3$;
wherein $R_{24}$ is hydrogen, $C_1$-$C_{20}$ alkyl optionally substituted with halo, hydroxyl, alkoxy, amino, alkylamino, dialkylamino, sulphate or phosphate; or aryl optionally substituted with halo, haloalkyl, hydroxyl, alkoxy, nitro, amino, alkylamino, dialkylamino, sulphate or phosphate; or
(iii) —$OSO_3H$, —$SO_3H$, —$PO_4$, —$PO_3H$, —COOH or a group represented by formula (B)

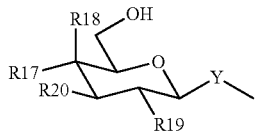

wherein:
Y is —O—, —$CH_2$— or —S—;
$R_{17}$, $R_{18}$, $R_{19}$ and $R_{20}$ are independently selected from —H, —OH, —$OSO_3H$, —$SO_3H$, —$PO_4$, —$PO_3H$, —NH—CO—$CH_3$ and —COOH; or
$R_{20}$ is a group represented by formula (B) wherein Y, $R_{17}$, $R_{18}$, $R_{19}$ and $R_{20}$ are as defined above;
or
(iv) N($R_9$)$R_{10}$ wherein
$R_9$ is (a) hydrogen or
(b) —$SO_2R_{11}$, wherein $R_{11}$ is:
halo; hydroxyl, $OR_{12}$, $OR_{13}$, amino, $NHR_{12}$, $N(R_{12})_2$, $NHR_{13}$, $N(R_{13})_2$, aralkylamino, or
$C_1$-$C_{12}$ alkyl optionally substituted with halo, hydroxyl, oxo, nitro, $OR_{12}$, $OR_{13}$, acyloxy, amino, $NHR_{12}$, $N(R_{12})_2$, $NHR_{13}$, $N(R_{13})_2$, aralkylamino, mercapto, thioalkoxy, $S(O)R_{12}$, $S(O)R_{13}$, $SO_2R_{12}$, $SO_2R_{13}$, $NHSO_2R_{12}$, $NHSO_2R_{13}$, sulphate, phosphate, cyano, carboxyl, $C(O)R_{12}$, $C(O)R_{13}$, $C(O)OR_{12}$, $C(O)NH_2$, $C(O)NHR_{12}$, $C(O)N(R_{12})_2$, $C_3$-$C_{10}$ cycloalkyl containing 0-3 $R_{14}$, $C_3$-$C_{10}$ heterocyclyl containing 0-3 $R_{14}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{15}$ or heteroaryl containing 0-3 $R_{15}$, or
$C_3$-$C_{10}$ cycloalkyl, $C_3$-$C_{10}$ heterocyclyl, $C_5$-$C_{10}$ cycloalkenyl, or $C_5$-$C_{10}$ heterocycloalkenyl optionally substituted with one or more halo, hydroxy, oxo, $OR_{12}$, $OR_{13}$, acyloxy, nitro, amino, $NHR_{12}$, $N(R_{12})_2$, $NHR_{13}$, $N(R_{13})_2$, aralkylamino, mercapto, thioalkoxy, $S(O)R_{12}$, $S(O)R_{13}$, $SO_2R_{12}$, $SO_2R_{13}$, $NHSO_2R_{12}$, $NHSO_2R_{13}$, sulphate, phosphate, cyano, carboxyl, $C(O)R_{12}$, $C(O)R_{13}$, $C(O)OR_{12}$, $C(O)NH_2$, $C(O)NHR_{12}$, $C(O)N(R_{12})_2$, alkyl, haloalkyl, $C_3$-$C_{10}$ cycloalkyl containing 0-3 $R_{14}$, $C_3$-$C_{10}$ heterocyclyl containing 0-3 $R_{14}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{15}$, or $C_6$-$C_{20}$ heteroaryl containing 0-3 $R_{15}$, or $C_2$-$C_6$ alkenyl, $C_2$-$C_6$ alkynyl, aryl or heteroaryl optionally substituted with one or more halo, hydroxy, $OR_{12}$, $OR_{13}$, acyloxy, nitro, amino, $NHR_{12}$, $N(R_{12})_2$, $NHR_{13}$, $N(R_{13})_2$, aralkylamino, mercapto, thioalkoxy, $S(O)R_{12}$, $S(O)R_{13}$, $SO_2R_{12}$, $SO_2R_{13}$, $NHSO_2R_{12}$, $NHSO_2R_{13}$, sulphate, phosphate, cyano, carboxyl, $C(O)R_{12}$, $C(O)R_{13}$, $C(O)OR_{12}$, $C(O)NH_2$, $C(O)NHR_{12}$, $C(O)N(R_{12})_2$, alkyl, haloalkyl, $C_3$-$C_{10}$ cycloalkyl containing 0-3 $R_{14}$, $C_3$-$C_{10}$ heterocyclyl containing 0-3 $R_{14}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{15}$, or $C_6$-$C_{20}$ heteroaryl containing 0-3 $R_{15}$, or -L-Ar wherein L is absent or a spacer moiety, preferably alkyl optionally interrupted by one carbonyl group or more, and Ar is an aromatic group optionally substituted, or
(c) —C(O)$R_{11}$, wherein $R_{11}$ is defined as above, or
(d) —C($R_{11}$)$_2$($R_{16}$), wherein $R_{11}$ is defined as above, $R_{16}$ is hydrogen, $R_{11}$, or $R_{16}$ and $R_{10}$ taken together form a double bond between the carbon and nitrogen atoms to which they are attached, or
(e) $R_9$ and $R_{10}$ taken together with N form a heterocycle of 3-10 ring atoms optionally substituted with $R_{11}$;

$R_{10}$ is hydrogen or $C_1$-$C_6$ alkyl, or $R_{10}$ and $R_{16}$ taken together form a double bond between the carbon and nitrogen atoms to which they are attached, or $R_{10}$ and $R_9$ taken together form a heterocyclyl of 3-10 ring atoms optionally substituted with $R_{11}$, $R_{12}$ is hydrogen or $C_1$-$C_{20}$ alkyl optionally substituted with halo, hydroxyl, alkoxy, amino, alkylamino, dialkylamino, sulphate or phosphate;

$R_{13}$ is aryl optionally substituted with halo, haloalkyl, hydroxyl, alkoxy, nitro, amino, alkylamino, dialkylamino, sulphate or phosphate, each $R_{14}$ is independently halo, haloalkyl, hydroxyl, alkoxy, oxo, amino, alkylamino, dialkylamino, sulphate or phosphate;

each $R_{15}$ is independently halo, haloalkyl, hydroxyl, alkoxy, nitro, amino, alkylamino, dialkylamino, sulphate or phosphate; and X is 1-100; or (v) a monosaccharide or an oligosaccharide;

$R_5$ is (i) —O—$R_{22}$, wherein $R_{22}$ is as defined above, or
(ii) —$NR_{24}$—CO—$CH_3$, wherein $R_{24}$ is as defined above or
(iii) —$OSO_3H$, —$SO_3H$; —$PO_4$, —$PO_3H$ or —COOH, or
(iv) —$OSO_3^-Na^+$;

$R_7$ is (i) —CH($OR_{18}$)$R_2$, or
(ii) —CH=CH($CH_2$)$R_2$, or
(iii) a linear or branched $C_3$-$C_{100}$ alkyl,
wherein $R_2$ is as defined above;

$R_{18}$ and $R_{23}$ are each independently hydrogen, $C_1$-$C_6$ alkyl, $C_6$-$C_{12}$ aralkyl or $C_1$-$C_6$ acyl;

R is —O—, —$CH_2$— or —S—.

Still preferably, the adjuvant according to the invention is a compound having the following formula (VII):

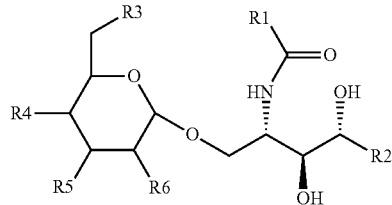

(VII)

wherein:
R$_1$ is
a) —(CH$_2$)$_X$CH$_3$ where X is an integer selected from 1 to 100; or
b) —(CH$_2$)$_X$CH=CH(CH$_2$)$_Y$CH$_3$ or —(CH$_2$)$_X$CH=CH(CH$_2$)$_Y$CH=CH(CH$_2$)$_Z$CH$_3$ wherein X, Y, and Z are integers independently selected from 1 to 14; and
R$_2$ is a linear or branched C$_3$-C$_{100}$ alkyl;
R$_3$, R$_4$, R$_5$ and R$_6$, identical or different, represent —OH or —NH—CO—CH$_3$, provided at least one of R$_3$ to R$_6$ represents —NH—CO—CH$_3$.

In said formulae (VI) and (VII), preferably, where R$_1$ is —(CH$_2$)$_X$CH$_3$, X is an integer selected from 18 to 26, still preferably from 22 to 24.

When R$_1$ is —(CH$_2$)$_X$CH=CH(CH$_2$)$_Y$CH$_3$ or —(CH$_2$)$_X$CH=CH(CH$_2$)$_Y$CH=CH(CH$_2$)$_Z$CH$_3$, X, Y, and Z are preferably integers independently selected from 5 to 14.

When R$_1$ is —(CH$_2$)$_X$CH=CH(CH$_2$)$_Y$CH$_3$, it may be preferred that X+Y be ≤23, preferably that 15≤X+Y≤23.

When R$_1$ is —(CH$_2$)$_X$CH=CH(CH$_2$)$_Y$CH=CH(CH$_2$)$_Z$CH$_3$, it may be preferred that X+Y+Z be ≤21, preferably that 13≤X+Y+Z≤21.

Also preferably, in formulae (VI) or (VII), R$_2$ is a linear or branched C$_{11}$-C$_{16}$ alkyl, still preferably a linear or branched C$_{14}$-C$_{16}$ alkyl, even more preferably a linear or branched C$_{14}$ alkyl.

More preferably, the derivative of galactosylceramide of the invention is an N-acetyl α-galactopyranosyl-lipid of the following formula (I)

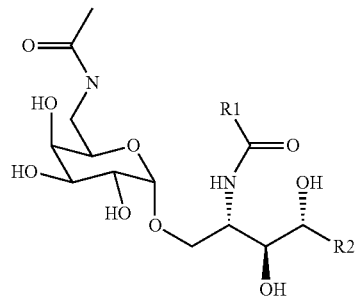

(I)

wherein R$_1$ and R$_2$ are as defined in formula (VII).

In a preferred embodiment, the adjuvant according to the invention is the compound called PBS-57 of following formula (II)

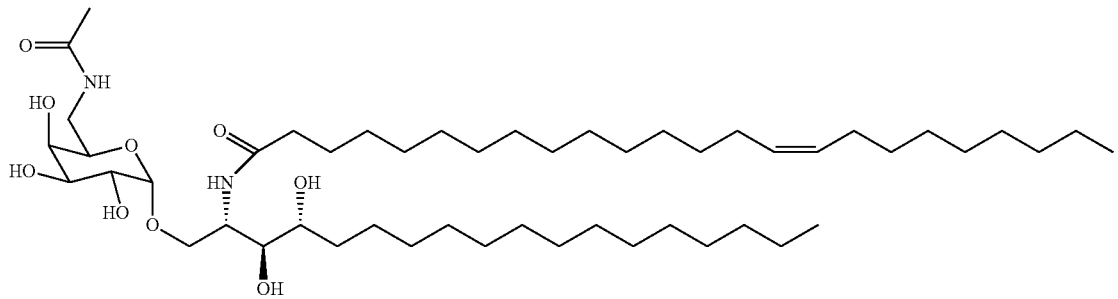

(II)

In another preferred embodiment, the adjuvant according to the invention is the compound called PBS-96 of following formula (III)

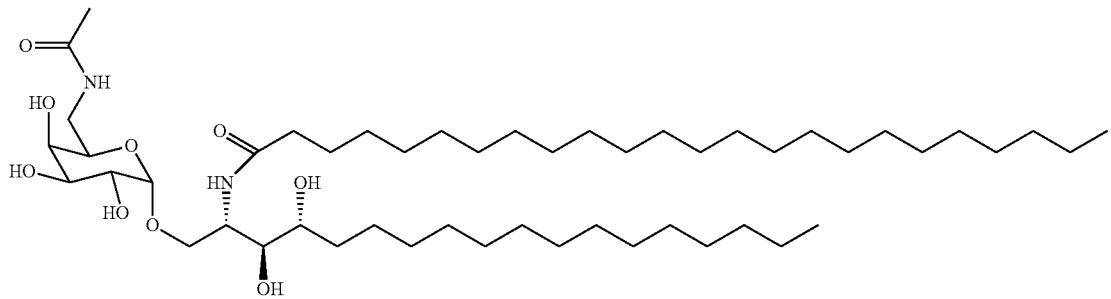

(III)

In another preferred embodiment, the adjuvant according to the invention is the compound called PBS-14 of following formula (IV)

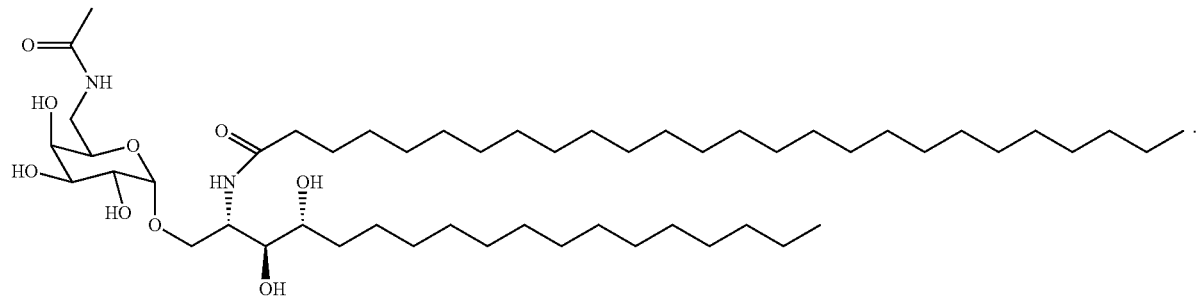

(IV)

When the adjuvant according to the invention corresponds to formula (I), it may further carry a PEG-2000 moiety linked to the amide moiety. Such compounds are for example the compound of following formula (VIII):

The term "acyl" refers to an alkylcarbonyl, cycloalkylcarbonyl, arylcarbonyl, heterocyclylcarbonyl or heteroarylcarbonyl substituent, any of which may be further substituted by substituents.

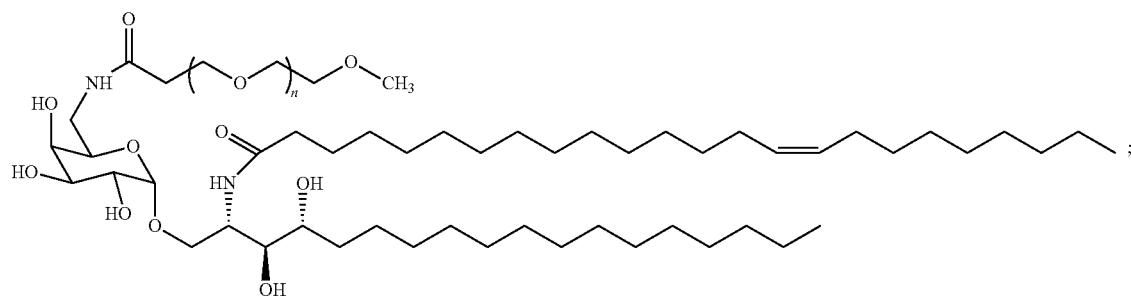

(VIII)

or the compound of following formula (IX):

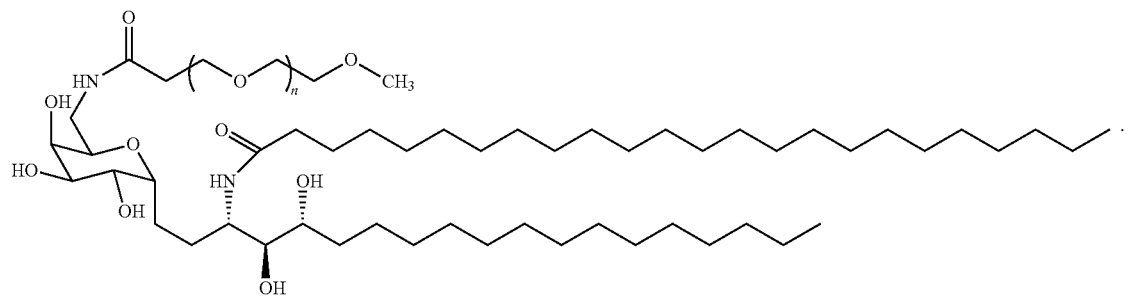

(IX)

As used herein, the term "alkyl" refers to a hydrocarbon chain that may be a straight chain or branched chain, containing the indicated number of carbon atoms. For examples, $C_3$-$C_{100}$ alkyl indicates that the group may have from 3 to 100 (inclusive) carbon atoms in it. The terms "arylalkyl" or "aralkyl" refer to an alkyl moiety in which an alkyl hydrogen atom is replaced by an aryl group. Examples of "arylalkyl" or "aralkyl" include benzyl and 9-fluorenyl groups.

The term "cycloalkyl" as employed herein includes saturated cyclic, bicyclic, tricyclic or polycyclic hydrocarbon groups having 3 to 12 carbons, wherein any ring atom capable of substitution can be substituted by a substituent. Examples of cycloalkyl moieties include, but are not limited to, cyclohexyl and adamantyl.

The term "aryl" refers to an aromatic monocyclic, bicyclic or tricyclic hydrocarbon ring system, wherein any ring atom capable of substitution can be substituted by a substituent.

Examples of aryl moieties include, but are not limited to, phenyl, naphtyl and anthracenyl.

The term "heterocyclyl" refers to a nonaromatic 3-10 membered monocyclic, 8-12 membered bicyclic or 11-14 membered tricyclic ring system having 1-3 heteroatoms if monocyclic, 1-6 heteroatoms if bicyclic or 1-9 heteroatoms if tricyclic, said heteroatoms being selected from O, N or S (e.g., carbon atoms and 1-3, 1-6 or 1-9 heteroatoms of N, O or S if monocyclic, bicyclic or tricyclic respectively), wherein any ring atom capable of substitution can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms being selected from O, N or S (e.g., carbon atoms and 1-3, 1-6 or 1-9 heteroatoms of N, O or S if monocyclic, bicyclic or tricyclic, respectively), wherein any ring atom capable of substitution can be substituted by a substituent.

The term "oxo" refers to an oxygen atom, which forms a carbonyl when attached to carbon, an N-oxide when attached to nitrogen, and a sulfoxide or sulfone when attached to sulphur.

The term "substituents" refers to a group "substituted" on an alkyl, cycloalkyl, heterocyclyl, aryl or heteroaryl group at any atom of that group. Suitable substituents include, without limitation, alkyl, alkenyl, alkynyl, alkoxy, halo, hydroxyl, cyano, nitro, amino, $SO_3H$, sulphate, phosphate, perfluoroalkyl, perfluoroalkoxy, methylenedioxy, ethylenedioxy, carboxyl, oxo, thioxo, imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl and combinations thereof), sulphonamide (mono-, di-, alkyl, aralkyl, heteroaralkyl and combinations thereof), unsubstituted aryl, unsubstituted heteroaryl, unsubstituted heterocyclyl and unsubstituted cycloalkyl.

The adjuvant according to the invention may be formulated under any suitable form, such as a suspension, a micro- or macro-emulsion, micelles, a depot formulation such as for depot injection, a dry formulation in particular suitable for topical and transdermal administration or in liposomes.

The adjuvant may also be formulated as a controlled release formulation, e.g. by combination with polymers such as PGA (polyglycolic acid) or with cyclodextrines.

The vaccine composition according to the invention may comprise one or several other adjuvant(s) in addition to the derivative of galactosylceramide adjuvant. The other adjuvants may be for instance a Toll-Like Receptor (TLR)-dependent adjuvant such as Ampligen (Hemispherx), AS01, AS02, AS04 (GSK); MPL (monophopshoryl lipid A) RC-529 (Dynavax), E6020 (Eisai/Sanofi Pasteur), TLR-technology (Vaxlnnate), CpG oligonucleotides in particular CpG 7909 (pfizer), ISS (Dynavax), IC31 (Intercell) and flagellin; or a TLR-independent adjuvant such as alum (e.g. aluminium hydroxide, aluminium phosphate), AS03 (GSK), MF59 (Novartis), Provax (Biogen Idec), Montanide (Seppic SA, Bioven, Cancervax), TiterMax (CytRx), Advax (Vaccine Pty), QS21 (purified saponin from Quillaja Saponaria; Antigenics, GSK), Quil A (Statens Serum Institute), ISCOMs (structured complex of saponins and lipids) and liposomes.

Indeed, the at least one prophylactically active agent against influenza may be an influenza vaccine as such, e.g. an authorised or under development influenza vaccine. Where the at least one prophylactically active agent against influenza is an influenza vaccine, it may already contain an adjuvant: e.g. Fluad® contains MF59, Focetria® contains MF59C.1 (mixture of squalene, polysorbate 80 sorbitan trioleate), Pandemrix® contains AS03 which is an adjuvant composed of squalene, DL-α-tocopherol and polysorbate 80.

Preferably, the vaccine composition according the invention further comprises at least one pharmaceutically acceptable carrier.

The term "pharmaceutically acceptable carrier" refers to a carrier that may be administered to a patient, together with a compound of this invention, and does not destroy the pharmacological activity thereof and is non-toxic when administered in doses sufficient to deliver a pharmaceutically effective amount of the compound.

Pharmaceutically acceptable carriers and vehicles that may be used in the vaccine compositions of this invention include, but are not limited to, ion exchangers, alumina, aluminium stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compositions according to the invention.

Preferably, at least one other adjuvant is included in the vaccine composition according to the invention, such as complete or incomplete Freud's adjuvant or aluminium hydroxide.

As appreciated by skilled artisans, vaccines are suitably formulated to be compatible with the intended route of administration. Examples of suitable routes of administration include parenteral, e.g., intravenous, intradermal, subcutaneous, intramuscular, intraperitoneal, oral (e.g., buccal, inhalation, nasal and pulmonary spray), intradermal, transdermal (topical), transmucosal, intraocular and rectal administration.

The vaccine composition according to the invention may be delivered in doses ranging from about 0.01 μg/Kg to about 5000 μg/Kg, alternatively from about 0.1 to about 1000 μg/Kg, alternatively from about 1 to about 500 μg/Kg. Effective doses will also vary depending on route of administration, as well as the possibility of co-usage with other agents.

The present invention also relates to a vaccine composition as defined above for use in the prevention or treatment of influenza.

"Preventing" or "prevention" of influenza as used herein refers to inhibiting infection, i.e. preventing the influenza virus from establishing an infection, or preventing spread of the influenza virus, i.e. to other areas of the subject, or from one subject to another.

"Treating" or "treatment" of influenza as used herein includes limiting disease severity, preventing recurrent infections, i.e. limiting reactivation of latent or persistent infections, and palliating symptoms of influenza.

In a preferred embodiment, the vaccine composition according to the invention is used in the treatment of influenza, wherein influenza is due to a first strain of an influenza virus, as defined above, and the at least one prophylactically agent active against influenza is selected from the group consisting of a live non-attenuated influenza virus, a live attenuated influenza virus, a killed or inactivated influenza virus, a subunit of an influenza virus, a recombinant polypeptide or protein, a cDNA or a recombinant influenza virus, as defined above, of a second strain of influenza virus, as defined above.

The present invention also relates to a method for treating or preventing influenza in a subject, comprising administering said subject with a prophylactically or therapeutic-effective quantity of a vaccine composition as defined above.

A "prophylactically or therapeutic-effective quantity" refers to a quantity of a vaccine composition that confers a prophylactic or therapeutic effect on the treated subject. The therapeutic effect may be objective (i.e., measurable by some test or marker) or subjective (i.e., subject gives an indication of or feels an effect). An effective amount of the vaccine composition described above may range from about 0.01 µg/Kg to about 5000 µg/Kg, alternatively from about 0.1 to about 1000 µg/Kg, alternatively from about 1 to about 500 µg/Kg. Effective doses will also vary depending on route of administration, as well as the possibility of co-usage with other agents.

In a preferred embodiment, the vaccine composition may be for use for inducing cross-protection against an influenza strain. Cross-protection is achieved when the vaccine composition prevents and/or treats an influenza infection due to a first strain of an influenza virus as defined above while the at least one prophylactically agent active against influenza is selected from the group consisting of a live non-attenuated influenza virus, a live attenuated influenza virus, a killed or inactivated influenza virus, a subunit of an influenza virus, a recombinant polypeptide or protein, a cDNA or a recombinant influenza virus, as defined above, of a second strain of an influenza virus, as defined above. Preferably, the at least one prophylactically agent active against influenza is from a seasonal influenza strain and the use of the adjuvant according to the invention makes it also effective against an influenza strain that is not in the prophylactically agent active against influenza. For example, the at least one prophylactically agent active against influenza is from an H1N1 influenza strain and is effective for the prevention and/or treatment of an influenza infection due to an H1N1 influenza strain and an influenza infection due to an influenza strain selected from the group consisting of H1N2, H2N2, H3N1, H3N2, H5N1 and H7N7. The at least one prophylactically agent active against influenza may be from an H1N2 influenza strain and is effective for the prevention and/or treatment of an influenza infection due to an H1N2 influenza strain and an influenza infection due to an influenza strain selected from the group consisting of H1N1, H2N2, H3N1, H3N2, H5N1 and H7N7. The at least one prophylactically agent active against influenza may be from an H2N2 influenza strain and is effective for the prevention and/or treatment of an influenza infection due to an H2N2 influenza strain and an influenza infection due to an influenza strain selected from the group consisting of H1N1, H1N2, H3N1, H3N2, H5N1 and H7N7. The at least one prophylactically agent active against influenza may be from an H3N1 influenza strain and is effective for the prevention and/or treatment of an influenza infection due to an H3N1 influenza strain and an influenza infection due to an influenza strain selected from the group consisting of H1N1, H1N2, H2N2, H3N2, H5N1 and H7N7. The at least one prophylactically agent active against influenza may be from an H3N2 influenza strain and is effective for the prevention and/or treatment of an influenza infection due to an H3N2 influenza strain and an influenza infection due to an influenza strain selected from the group consisting of H1N1, H1N2, H2N2, H3N1, H5N1 and H7N7. The at least one prophylactically agent active against influenza may be from an H5N1 influenza strain and is effective for the prevention and/or treatment of an influenza infection due to an H5N1 influenza strain and an influenza infection due to an influenza strain selected from the group consisting of H1N1, H1N2, H2N2, H3N1, H3N2 and H7N7. The at least one prophylactically agent active against influenza may be from an H7N7 influenza strain and is effective for the prevention and/or treatment of an influenza infection due to an H7N7 influenza strain and an influenza infection due to an influenza strain selected from the group consisting of H1N1, H1N2, H2N2, H3N1, H3N2 and H5N1. Typically, the at least one prophylactically agent active against influenza is from an H1N1 or an H3N2 influenza strain and is effective for the prevention and/or treatment of an influenza infection due to an H1N1 or H3N2 influenza strain and an influenza infection due to an H5N1 or H3N8 influenza strain.

Additionally, the adjuvant according to the invention has the property of increasing the efficiency of the at least one prophylactically agent active against influenza. In particular, the use of the adjuvant according to the invention enables to decrease the number of administered doses of prophylactically agent active against influenza. For example, an administration of one dose of vaccine according to the invention comprising the prophylactically agent active against influenza with the adjuvant according to the invention is as efficient as the administration of two doses of vaccine comprising the prophylactically agent active against influenza without the adjuvant according to the invention. Similarly, an administration of one or two doses of vaccine according to the invention comprising the prophylactically agent active against influenza with the adjuvant according to the invention is as efficient as the administration of three doses of vaccine comprising the prophylactically agent active against influenza without the adjuvant according to the invention. The use of the adjuvant according to the invention also enables to decrease the dose of the prophylactically agent active against influenza.

The adjuvant according to the invention also has the property of activating cytotoxic T lymphocytes against the influenza epitope, in particular inducing a Th1 response, whereas the at least one prophylactically agent active against an influenza virus alone only increases IgG production.

Furthermore, whereas the prophylactically agent active against influenza usually used in vaccines are less efficient in children (i.e. a human being who is from birth to 18 years old) and in the elderly (i.e. a human being who is 65 years old or above), the adjuvant according to the invention increases the efficiency of said prophylactically agent active against influenza in children and in the elderly.

The invention is further illustrated by the following figures and examples.

BRIEF DESCRIPTION OF THE FIGURES

FIG. 17 shows a graph representing the number of living mice after no immunisation (control), an immunization with Fluarix®, PBS-96 or Fluarix®+PBS-96 and an infection with H5N1, or after an immunisation with mock and no infection (mock).

EXAMPLES

Figure 1:
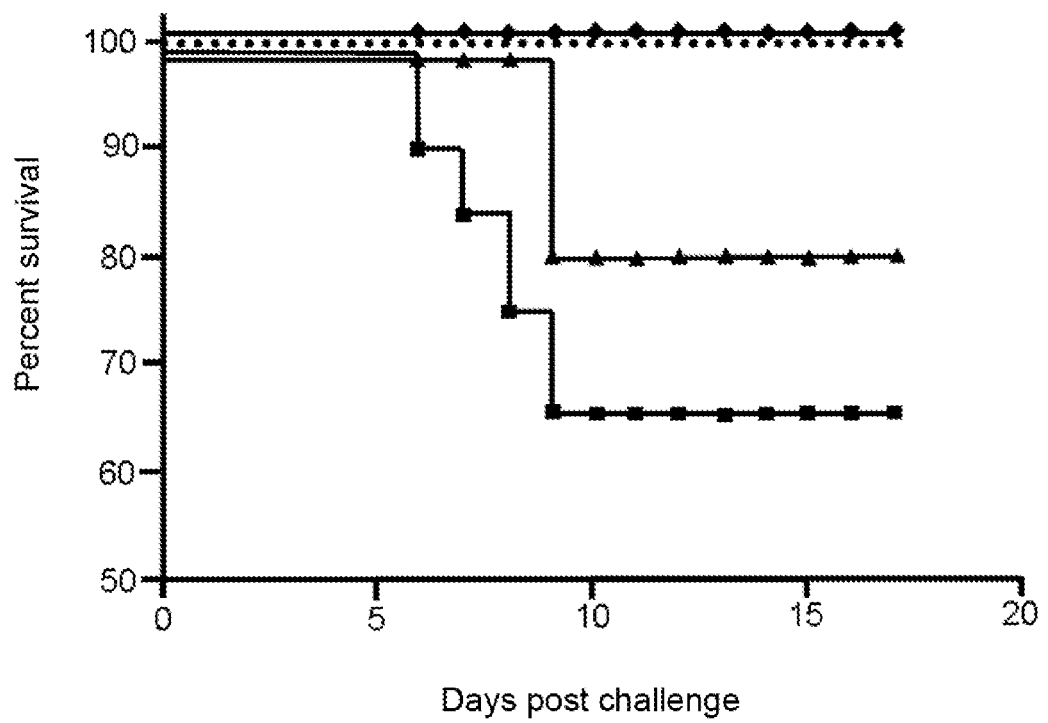
FIG. 1 shows a graph representing the percent survival among mice, unchallenged (dotted line), challenged with the H3N8 influenza virus strain without prior immunization (■), after immunization with the influenza vaccine Protec-Flu®, alone (▲) or with 1 µg of PBS-57 (♦) at different days post challenge.

The following examples highlight the increased protection and cross-protection against influenza virus obtained by using N-acetylglycolipids in vaccine compositions.

Example 1

Increase in Mice Survival and Cross-Protection Induced by N-acetylglycolipid Adjuvants Materials and Methods Two different vaccines were used in the experiments.
- the commercial human vaccine Agrippal® (purchased from Novartis) which is obtained namely from the H1N1 Influenza A strain, and
- the commercial horse vaccine Equi Protec-Flu® (purchased from Merial) which is obtained from the H3N8 Influenza A strain.

0.5 ml of each vaccine was diluted at 1/10,000 in NaCl 0.9% solution before use.

Respectively 100 μl of liposome PBS-57 preparation, liposome PBS-96 preparation, or liposome PBS-14 preparation at 1 mg/ml was diluted at 1/10 in NaCl 0.9% solution. 110 μl of this dilution was then added to 440 μl of each vaccine preparation, so that respectively 1 μg of PBS-57, of PBS-96 or of PBS-14 was contained in 50 μl of each vaccine preparation.

For control, 100 μl of liposome preparation was diluted at 1/5 in NaCl 0.9% solution. 110 μl of this dilution was then added to 440 μl of each vaccine preparation.

3 to 4 week-old weaned female mice of C57Bl/6 strain were randomly assigned to one of the 9 treatment groups. Mice were acclimatized for less than 5 days and received treatment as followed:
- group 1: unchallenged control
- group 2: challenged untreated
- group 3: Agrippal® only
- group 4: Agrippal®+1 µg PBS-57
- group 5: Agrippal®+1 µg PBS-96
- group 6: Agrippal®+1 µg PBS-14
- group 7: Protec-Flu® only
- group 8: Protec-Flu®+1 µg PBS-57
- group 9: Protec-Flu®+1 µg PBS-14

Equine H3N8 virus (A/Equine/2/Miami/1/63 (ATCC-VR-317) obtained from Pasteur Institute, Paris, France) was used in viral challenges. Animals received intravenously 100 µl of influenza inoculum preparation.

The treatment scheme was as follows:
- on day 0, the vaccine (control, Agrippal® or Protec-Flu®) was injected by intramuscular route to the mice, with or without the tested adjuvant.
- on day 7, the H3N8 virus was injected by intravenous route to the mice.
- on days 21 to 24 (14 to 17 post challenge), the health and weight of the mice were monitored, and the survival and morbidity rates were evaluated.

Results

At day 10 post challenge, about 60% of untreated mice which had been challenged with the H3N8 virus strain survived.

Figure 3:
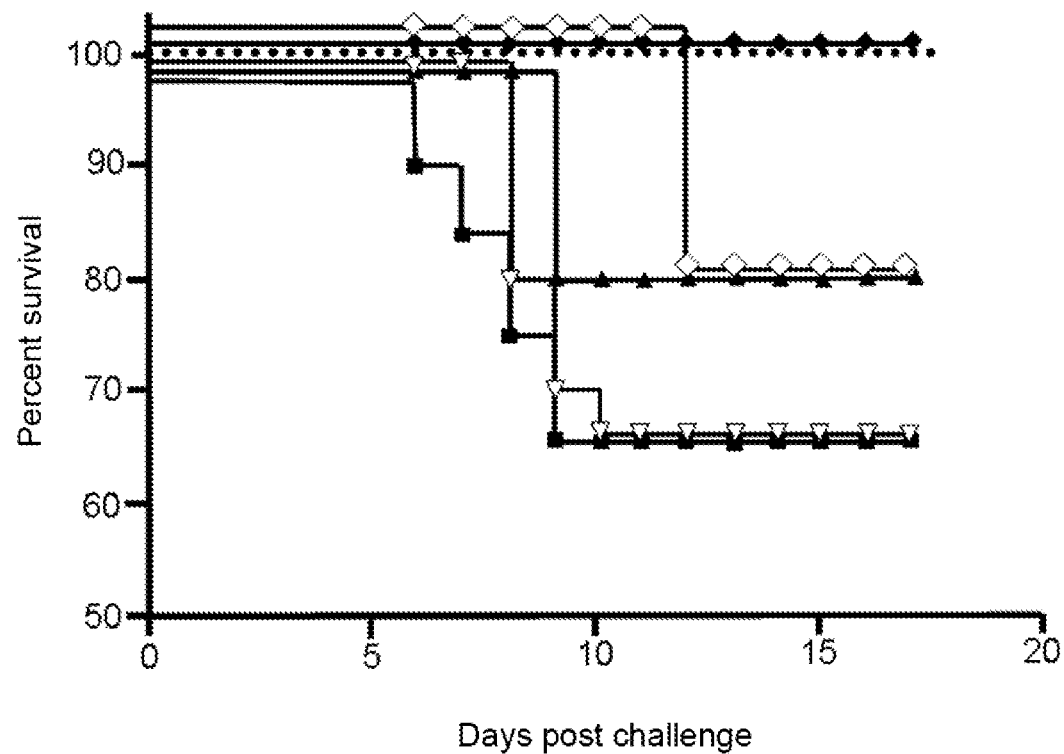
FIG. 3 shows a graph representing the percent survival among mice, unchallenged (dotted line), challenged with the H3N8 influenza virus strain without prior immunization (■), after immunization with the influenza vaccine Protec-Flu®, alone (▲) or with 1 μg of PBS-14 (♦), or after immunization with the influenza vaccine Agrippal®, alone (∇) or with 1 μg of PBS-14 (◇), at different days post-challenge.

Among mice that had been treated with the Protec-Flu® vaccine (obtained from the H3N8 strain), at day 15 post-challenge, only 80% of mice treated with Protec-Flu® alone were alive, whereas 100% of mice treated with Protec-Flu®+PBS-57 and of mice treated with Protec-Flu®+PBS-14 were still alive (FIGS. 1 and 3).

The inventors thus demonstrated that the use of N-acetylglycolipids increased considerably the efficacy of the influenza virus vaccine.

Figure 2:
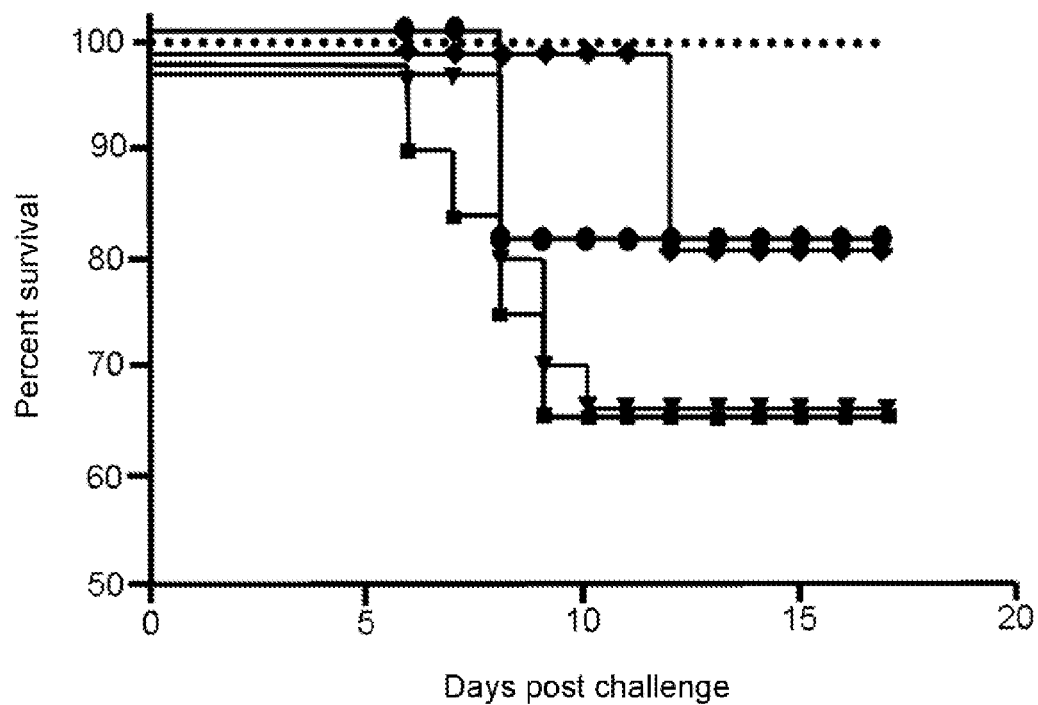
FIG. 2 shows a graph representing the percent survival among mice, unchallenged (dotted line), challenged with the H3N8 influenza virus strain without prior immunization (■), after immunization with the influenza vaccine Agrippal®, alone (▼) or with 1 μg of PBS-57(♦) or 1 μg of PBS-96 (●), at different days post challenge.

Among mice that had been treated with the Agrippal® vaccine (obtained namely from the H1N1 strain), at day 15 post challenge, only 65% of mice treated with Agrippal® alone were alive, whereas 80% of mice treated with Agrippal®+PBS-96, of mice treated with Agrippal®+PBS-57 and of mice treated with Aggripal®+PBS-14 were still alive (FIGS. 2 and 3).

Accordingly, the inventors demonstrated that the use of the N-acetylglycolipids PBS-57, PBS-96 and PBS-14 not only increased the efficacy of the influenza virus vaccine but also enabled to protect animals against an influenza strain different from the one used to manufacture the vaccine.

Example 2

Detection of IgG1, IgG2a and IgG2b in Mouse Sera After Intramuscular Administration of Agrippal® Vaccine and N-acetylglycolipid Adjuvants Mice were injected at day 0 and day 21 with:
PBS,
1 µg Agrippal® alone,
1 µg Agrippal®+1 µg PBS-57 in pegylated form or liposome formulation (PBS-57/S or PBS-57/L) or PBS-14 liposome formulation (PBS-14/L),
4 µg Agrippal® alone,
4 µg Agrippal®+1 µg PBS-57/S or PBS-57/L or PBS-14/L,
8.9 µg Agrippal® alone, or
8.9 µg Agrippal®+1 µg PBS-57/S or PBS-57/L or PBS-14/L.

Figure 4:
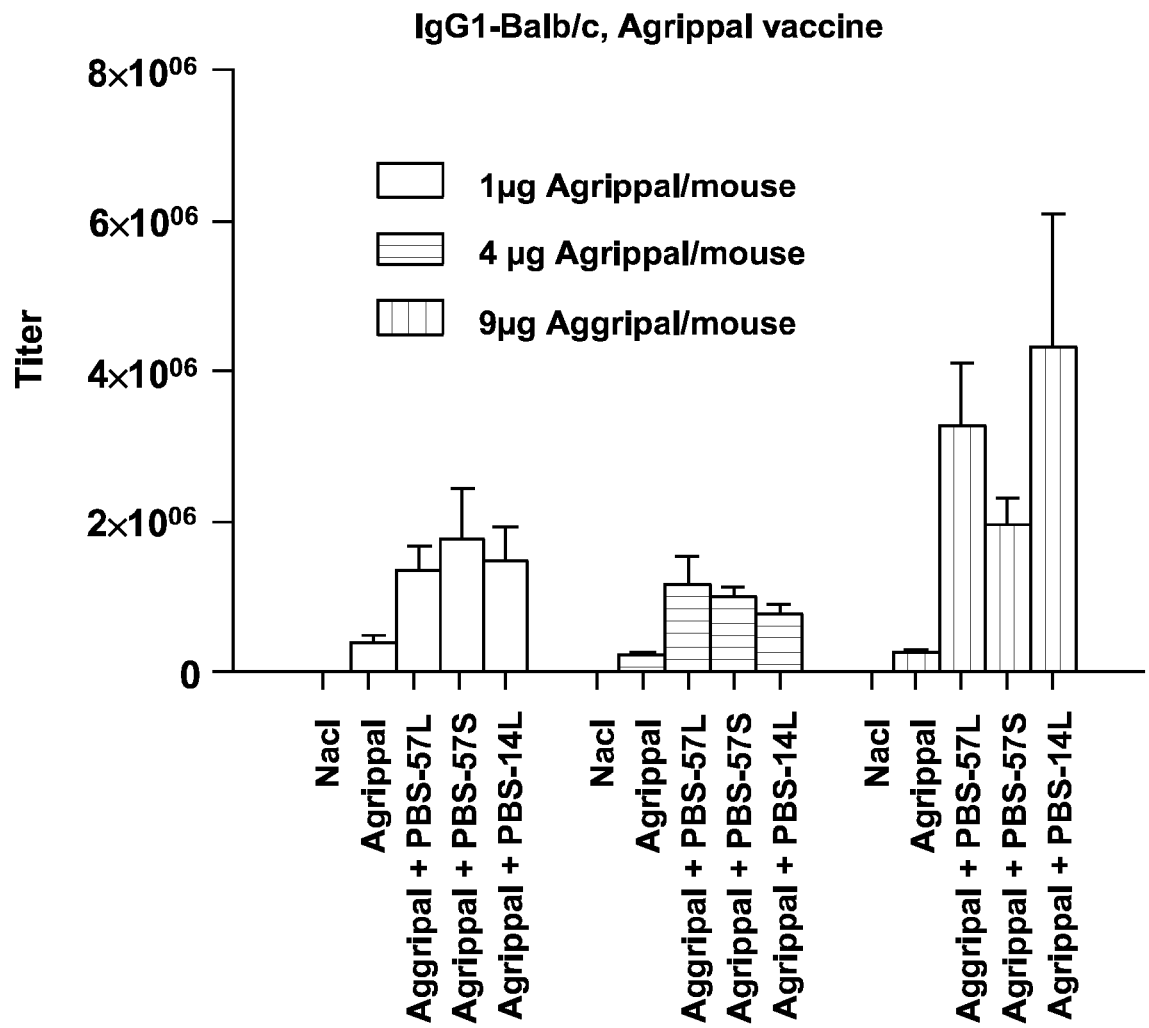
FIG. 4 shows the level of IgG1 detected in the sera of mice immunised twice with PBS alone, Agrippal® vaccine alone, or Agrippal® vaccine combined with PBS-57 or PBS-14 adjuvant (/S: PEGylated form; /L: liposome). The experiments were made with 1, 4 or 9 μg Aggripal® vaccine per mouse.
Figure 5:
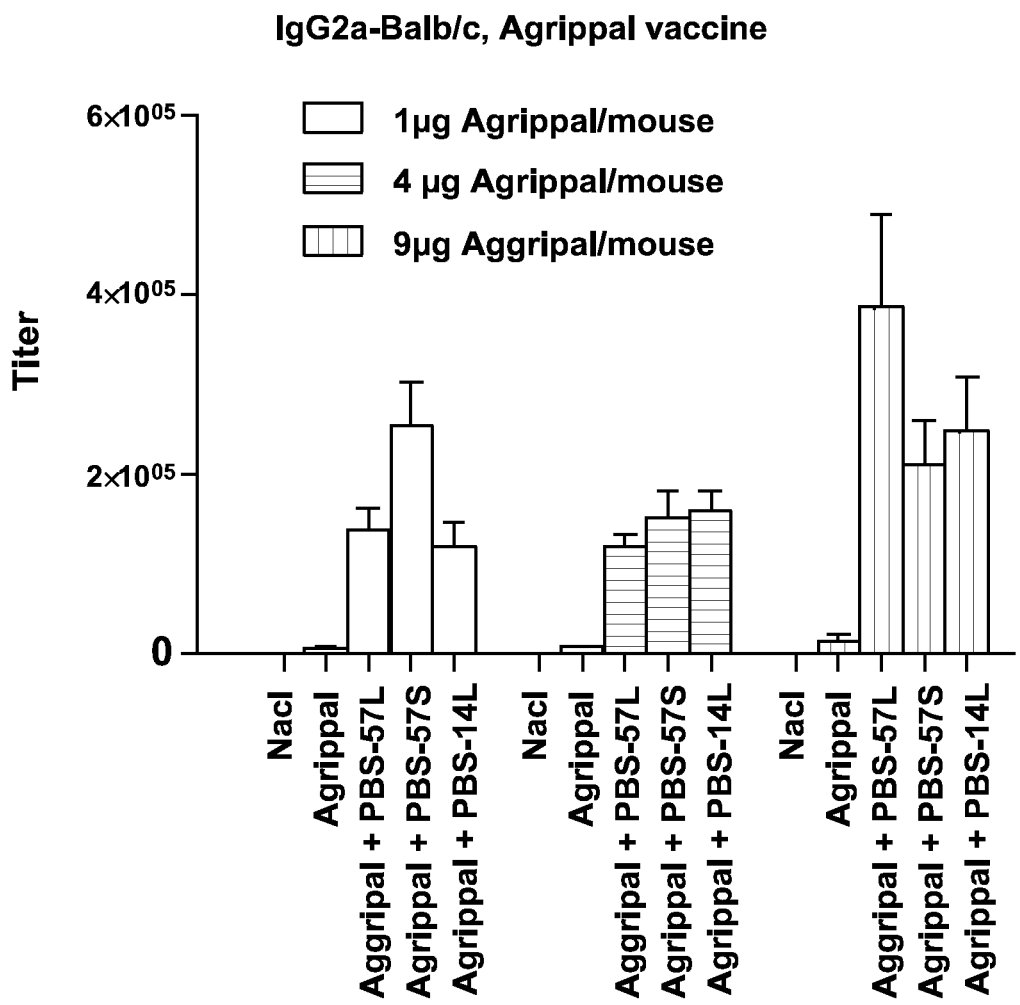
FIG. 5 shows the level of IgG2a detected in the sera of mice immunised twice with PBS alone, Agrippal® vaccine alone, or Agrippal® vaccine combined with PBS-57 or PBS-14 adjuvant (/S: PEGylated form; /L: liposome). The experiments were made with 1, 4 or 9 μg Aggripal® vaccine per mouse.
Figure 6:
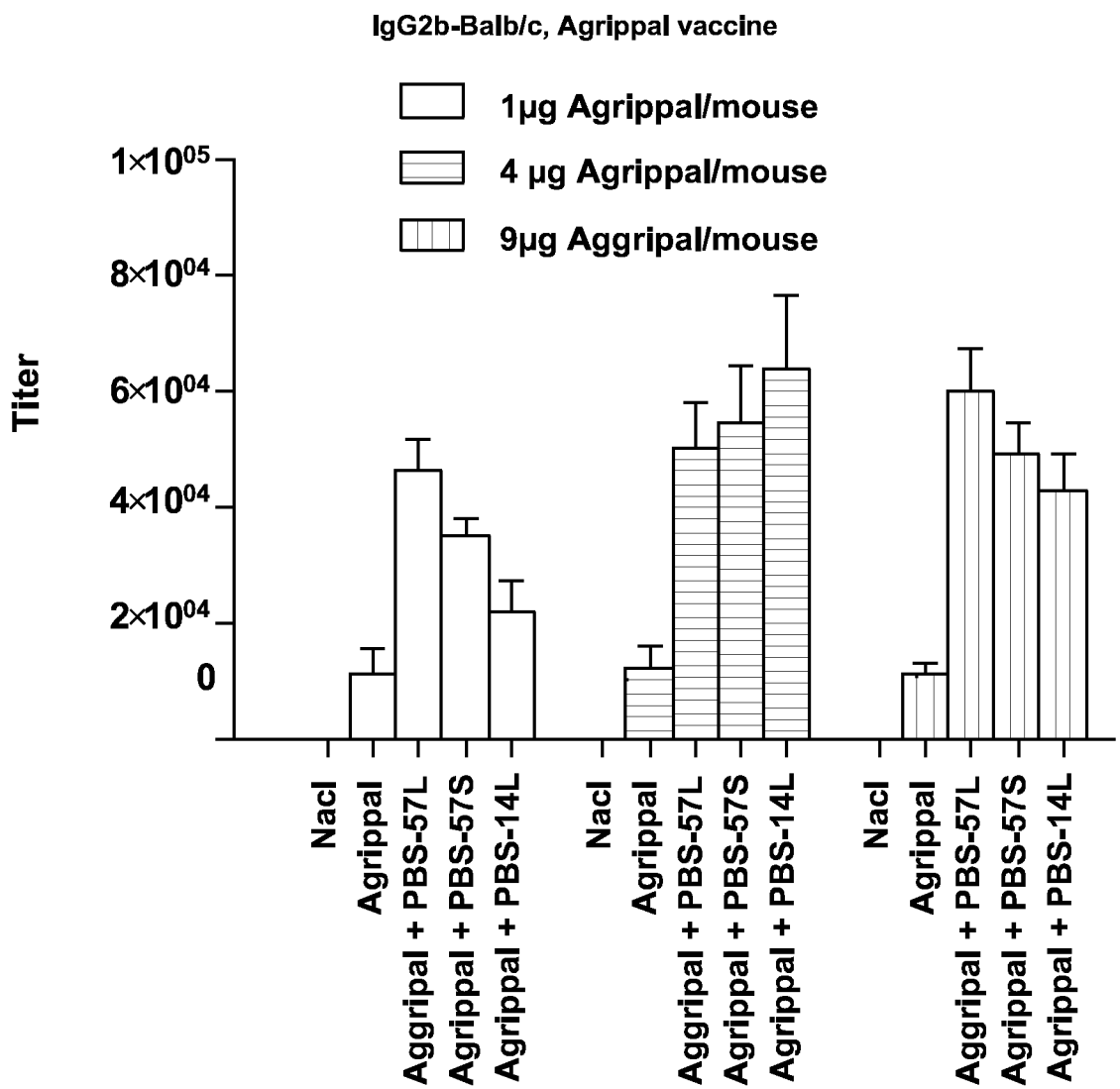
FIG. 6 shows the level of IgG2b detected in the sera of mice immunised twice with PBS alone, Agrippal® vaccine alone, or Agrippal® vaccine combined with PBS-57 or PBS-14 adjuvant (/S: PEGylated form; /L: liposome). The experiments were made with 1, 4 or 9 μg Aggripal® vaccine per mouse.

Sera were collected at day 42 and the IgG1, IgG2a and IgG2b content of the sera was analysed by ELISA. Results are displayed on FIGS. 4 to 6. The analyses show that whereas increased levels of Agrippal®, when administered alone, do not enhance the level of IgG1, IgG2a and IgG2b produced, the combination of Agrippal® with PBS-57 or PBS-14, even with the lowest dose of Agrippal®, increases the amount of detectable IgG1, IgG2a and IgG2b. Noteworthy, the levels of IgG1, IgG2a and IgG2b were not significantly further increased when the dose of Agrippal® combined to PBS-57 or PBS-14 was increased.

Example 3

Indirect Hemagglutination Assay (IHA) Testing of Mice Sera by Intramuscular Route Immunized Twice with Fluarix®

Mice were injected by intramuscular route at day 0 and day 21 with:
NaCl,
1 µg Fluarix® alone,
1 µg Fluarix®+1 µg PBS-57/S, or
1 µg Fluarix®+1 µg PBS-57/L.

Fluarix® vaccine comprises a mixture of A/Brisbane/10/2007-like, A/Brisbane/59/2007-like, and B/Florida/4/2006-like strains.

Figure 7:
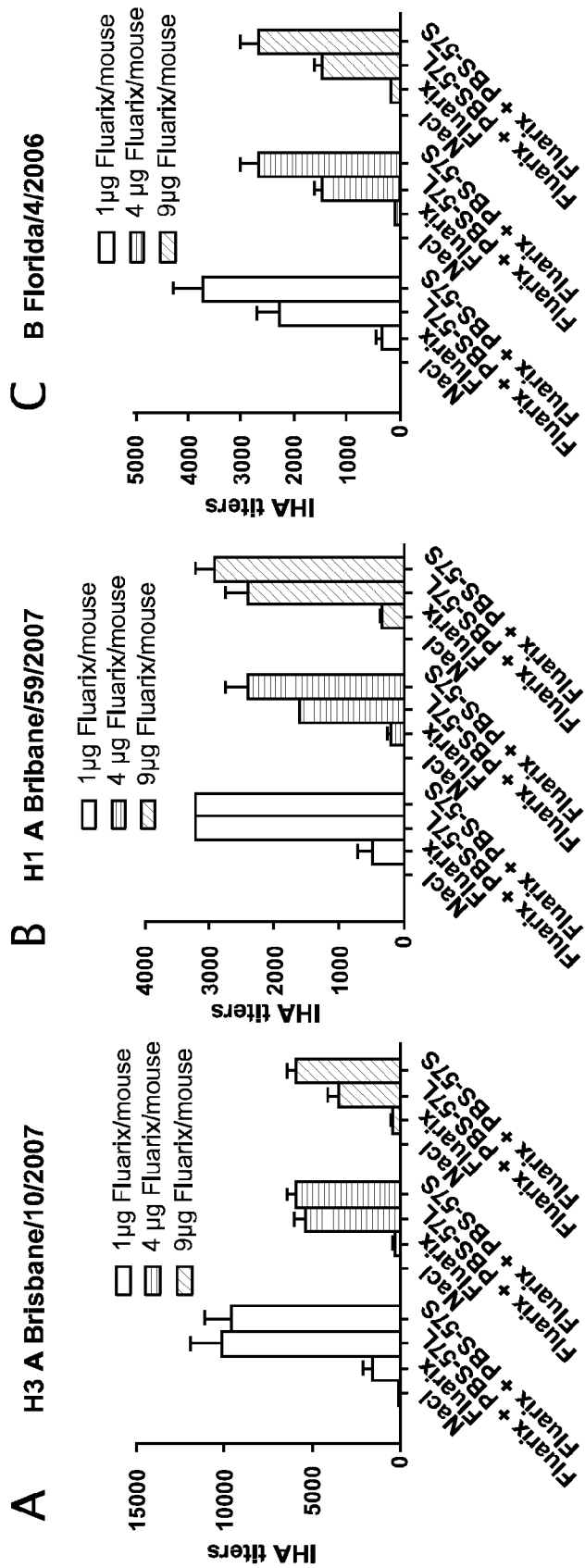
FIG. 7 shows IHA (indirect hemagglutination assay) titers measured in mice immunised twice with 1 μg Fluarix® vaccine alone or 1 μg Fluarix® vaccine combined with PBS-57/S or PBS-57/L (/S: PEGylated form; /L: liposome). A: IHA titer for strain A/Brisbane/10/2007; B: IHA titer for strain A/Brisbane/59/2007; C: IHA titer for strain B/Florida/4/2006. The experiments were made with 1, 4 or 9 μg Fluarix® vaccine per mouse.

Sera were collected at day 42 and reactivity with the three prototypical strains (A/Brisbane/10/2007, A/Brisbane/59/2007, and B/Florida/4/2006) of Fluarix® vaccine was assayed by measuring IHA titers for each of these strains (see FIG. 7).

It was found that PBS-57, whether in solution or liposome formulation, significantly enhanced IHA titers induced by Fluarix® vaccination against A/Brisbane/10/2007 and B/Florida/4/2006 strains (Table 1). IHA titers against A/Brisbane/59/2007 strain were also enhanced but to a less significant level.

TABLE 1

Level of significance of enhanced IHA titers induced by PBS-57

| | | | | | |
|---|---|---|---|---|---|
| A/Brisbane/10/2007 | 1 µg Fluarix | vs | 1 µg Fluarix ® + PBS-57/S | P | 0.0004 *** |
| A/Brisbane/10/2007 | 1 µg Fluarix | vs | 1 µg Fluarix ® + PBS-57/L | P | 0.0008 *** |
| B/Florida/4/2006 | 1 µg Fluarix | vs | 1 µg Fluarix ® + PBS-57/S | P | <0.0001 *** |
| B/Florida/4/2006 | 1 µg Fluarix | vs | 1 µg Fluarix ® + PBS-57/L | P | 0.0015 ** |

The same results were obtained with PBS-14 and PBS-96.

Example 4

Indirect Hemagglutination Assay (IHA) Testing of Mice Sera Immunized Twice with Agrippal®

Mice were injected by intramuscular route at day 0 and day 21 with:
nothing (naïve mice),
PBS,
4 µg Agrippal® alone,
8.9 µg Agrippal® alone, 4 µg Agrippal®+1 µg PBS-57 in liposome formulation (PBS-57/L) or PBS-14 liposome formulation (PBS-14/L), or 8.9 µg Agrippal®+1 µg PBS-57 in PEGylated form (PBS-57/S) or PBS-57/L or PBS-14/L.

Agrippal® vaccine comprises a mixture of A/Brisbane/10/2007-like, A/Brisbane/59/2007-like, and B/Florida/4/2006-like strains.

Figure 8:
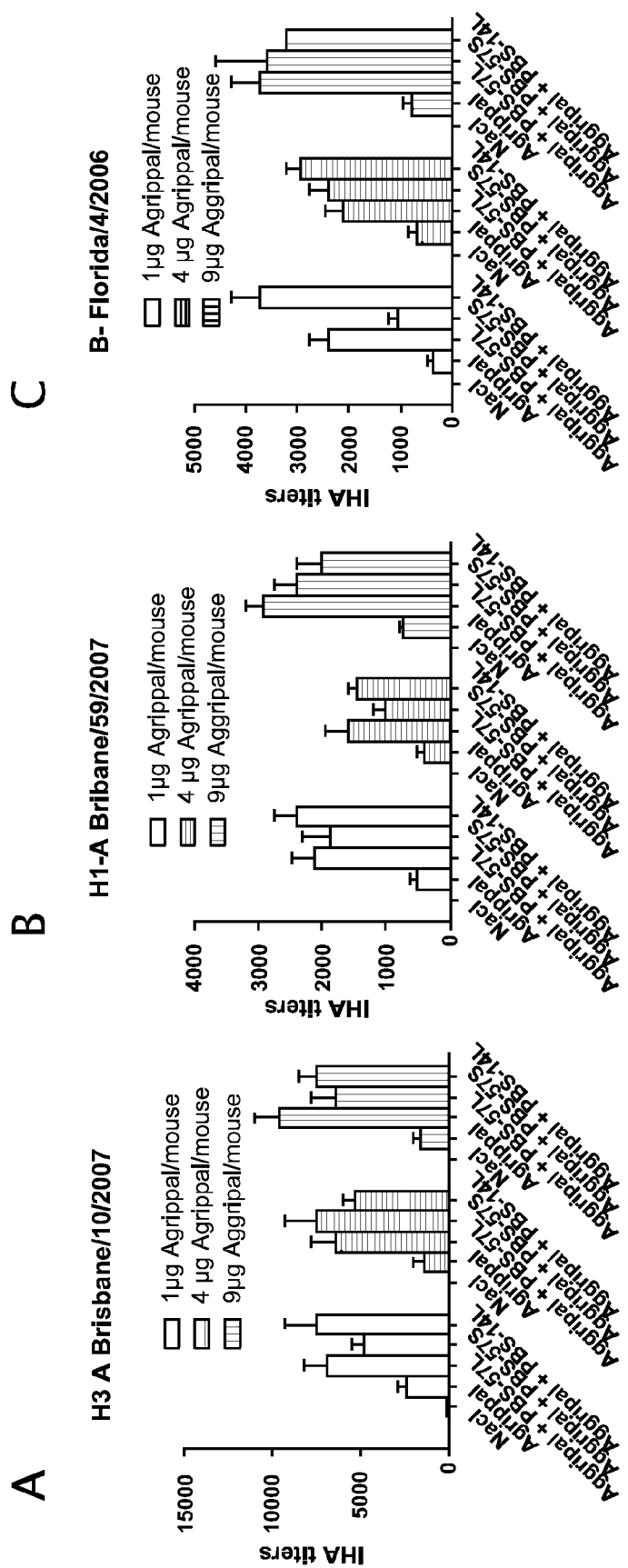
FIG. 8 shows IHA (indirect hemagglutination assay) titers measured in mice immunised twice with 4 μg or 8.9 μg Agrippal® vaccine alone or combined with PBS-57/S, PBS-57/L or PBS-14/L (/S: PEGylated form; /L: liposome). A: IHA titer for strain A/Brisbane/10/2007; B: IHA titer for strain A/Brisbane/59/2007; C: IHA titer for strain B/Florida/4/2006. The experiments were made with 1, 4 or 9 μg Aggripal® vaccine per mouse.

Sera were collected at day 42 and reactivity with the three prototypical strains (H3 A/Brisbane/10/2007, H1 A/Brisbane/59/2007, and B/Florida/4/2006) of Agrippal® vaccine was assayed by measuring IHA titers for each of these strains (see FIG. 8).

It was found that PBS-57 and PBS-14 increased IHA titers as compared with the Agrippal® vaccine alone (Table 2).

TABLE 2

Level of significance of enhanced IHA titers induced by PBS-57 and PBS-14

| Virus | | Vs | P | * |
|---|---|---|---|---|
| H3 | 4 µg Agrippal ® | 4 µg Agrippal ® + PBS-57/S | 0.0088 | ** |
| H3 | 4 µg Agrippal ® | 4 µg Agrippal ® + PBS-57/L | 0.0086 | ** |
| H3 | 4 µg Agrippal ® | 4 µg Agrippal ® + PBS-14/L | 0.0013 | ** |
| H1 | 4 µg Agrippal ® | 4 µg Agrippal ® + PBS-57/S | 0.0241 | * |
| H1 | 4 µg Agrippal ® | 4 µg Agrippal ® + PBS-57/L | 0.0094 | ** |
| H1 | 4 µg Agrippal ® | 4 µg Agrippal ® + PBS-14/L | <0.0001 | *** |
| B | 4 µg Agrippal ® | 4 µg Agrippal ® + PBS-57/S | 0.0017 | ** |
| B | 4 µg Agrippal ® | 4 µg Agrippal ® + PBS-57/L | 0.0038 | ** |
| B | 4 µg Agrippal ® | 4 µg Agrippal ® + PBS-14/L | <0.0001 | *** |

The same results were obtained with PBS-96.

Example 5

Indirect Hemagglutination Assay (IHA) Testing of Mice Sera Immunized Once with Agrippal®

Mice were injected by intramuscular route at day 0 with:
NaCl,
PBS-57/D alone,
PBS-57/L alone,
PBS-57/S alone,
4 µg Agrippal® alone,
8.9 µg Agrippal® alone,
4 µg Agrippal®+1 µg PBS-57 in liposome formulation (PBS-57/L) or in pegylated form (PBS-57/S) or in DMSO (PBS-57/D), or
8.9 µg Agrippal®+1 µg PBS-57/L or PBS-57/S or PBS-57/D.

Figure 9:
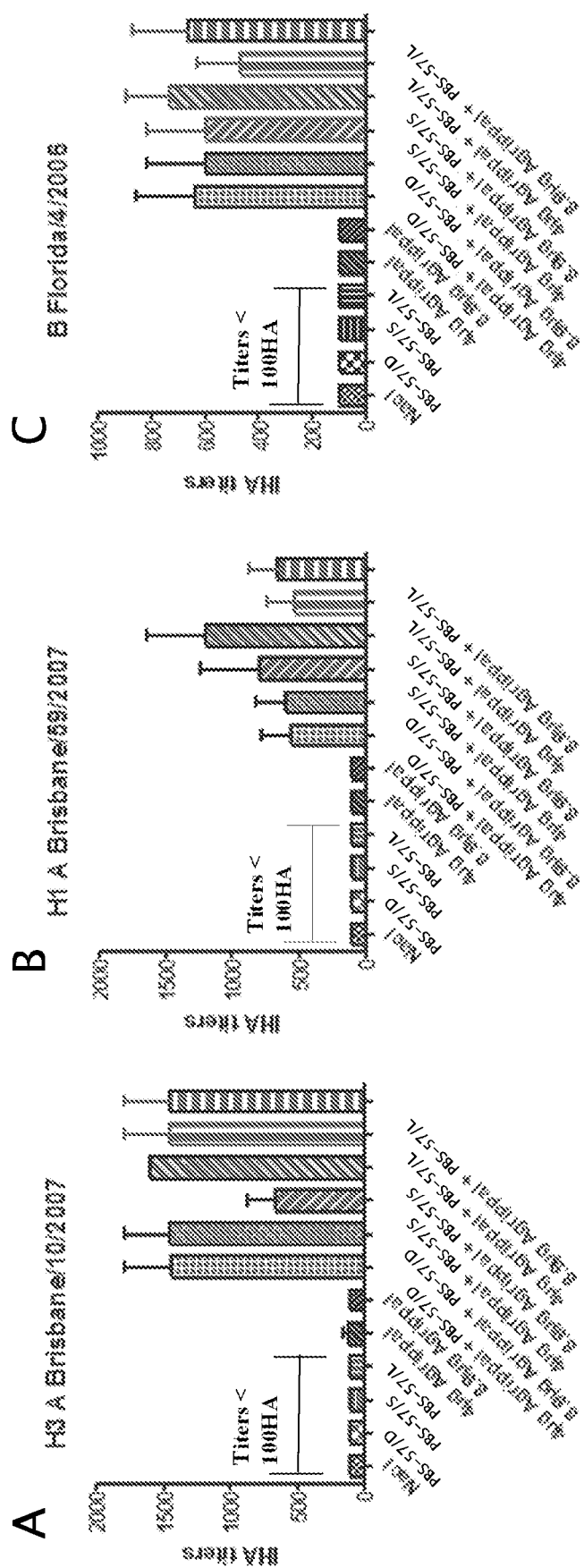
FIG. 9 shows IHA (indirect hemagglutination assay) titers measured in mice immunised once with 4 μg or 8.9 μg Agrippal® vaccine alone or combined with PBS-57/S, PBS-57/L or PBS-57/D (/S: PEGylated form; /L: liposome; /D: DMSO). A: IHA titer for strain A/Brisbane/10/2007; B: IHA titer for strain A/Brisbane/59/2007; C: IHA titer for strain B/Florida/4/2006.

Sera were collected at day 21 and reactivity with the three prototypical strains (H3 A/Brisbane/10/2007, H1 A/Brisbane/59/2007, and B/Florida/4/2006) of Agrippal® vaccine was assayed by measuring IHA titers for each of these strains (see FIG. 9). PBS-57 and PBS-14 increased IHA titers as compared with the Agrippal® vaccine alone after a single injection.

TABLE 3

Level of significance of enhanced IHA titers induced by PBS-57

| H3 | Vs | p | * |
|---|---|---|---|
| 4 µg Agrippal ® | 4 µg Agrippal ® + PBS-57/D | <0.0001 | *** |
| 4 µg Agrippal ® | 4 µg Agrippal ® + PBS-57/S | <0.0001 | *** |
| 4 µg Agrippal ® | 4 µg Agrippal ® + PBS-57/L | <0.0001 | *** |

These results show that the adjuvants avoid prime boost vaccination in seasonal flu.

Example 6

Activation of Specific T Cell in Mice Immunized with Fluarix® and PBS-57

Mice were immunised by intramuscular route with 4 µg or 9 µg HA antigen in combination or not with PBS-57 (1 µg). H-2 Kb NP (ASNENME™; SEQ ID NO: 1)-specific CD8+ T cells were monitored in the blood at different time points by multimeric peptide/class I complexes analyses.

Figure 10:
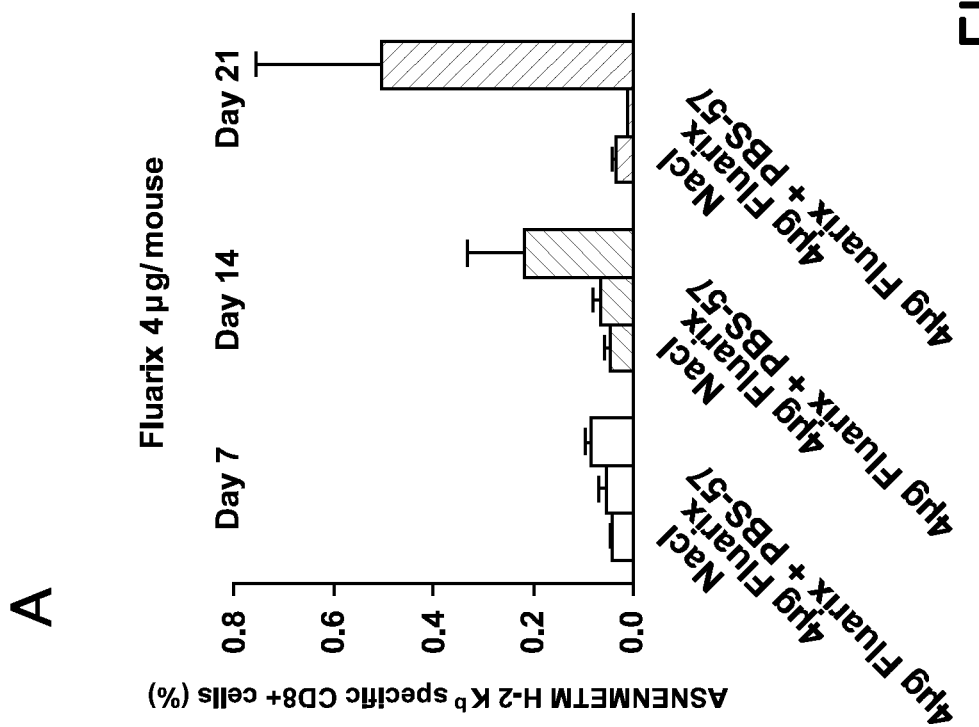
FIG. 10 shows pentamer specific CD8$^+$ T cell responses in blood of mice immunised with 4 μg (left panel) or 9 μg (right panel) Fluarix® vaccine alone, or combined with PBS-57. T cell responses were observed 7, 14 or 21 days after the immunization.
Figure 10:
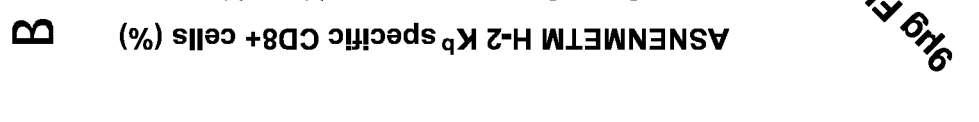

Highest expansion of H-2 Kb NP-specific CD8+ T cells was found in vaccinated animals, 14 days following immunisation, with PBS-57, at the doses tested (FIG. 10). On days 21 after the priming, the frequency of these cells in the blood was steady, as compared to day 14.

The same results were obtained with PBS-14 and PBS-96, and with Aggripal® instead of Fluarix®.

Example 7

Vaccination Flu Challenge Model

A study similar to the one presented in Example 1 was performed by the inventors but in more drastic conditions and under a higher number of conditions.

a) Immunization Protocol

Balb/c mice were injected at day 0 by intramuscular route with Fluarix® 1/30,000 or Agrippal® 1/30,000 optionally combined with PBS-14/L, PBS-57-L or PBS-96/L. The concentrations of Fluarix® and Agrippal® were selected to achieve 50% survival over the period of monitoring when the flu vaccine is administered alone.

At day 21, anesthetized mice were inoculated by intranasal route with a H3N8 strain with high pathogenicity (0% survival in the group of untreated mice challenged with the virus).

From day 21 to day 35, health and weight of the mice were monitored and the survival and morbidity rates were determined.

b) Results

Figure 11:
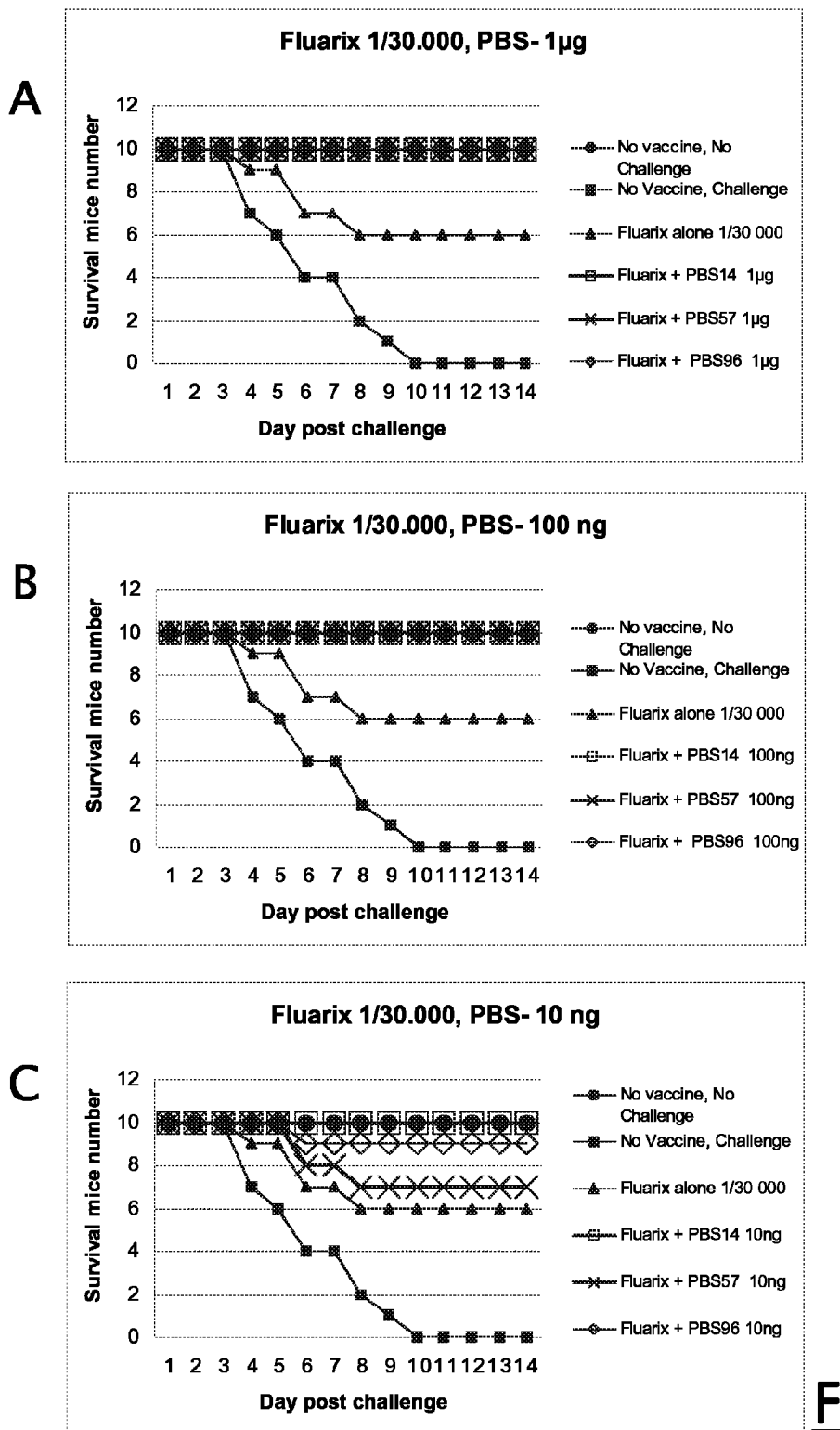
FIG. 11 shows survival of mice in a flu challenge model with a highly pathogenic H3N8 strain. Mice were vaccinated at day 0 with Fluarix® 1/30,000 and PBS-14, PBS-57 or PBS-96 liposomes 1 μg (A), 100 ng (B) or 10 ng (C), and were challenged at day 21 with H3N8.
Figure 12:
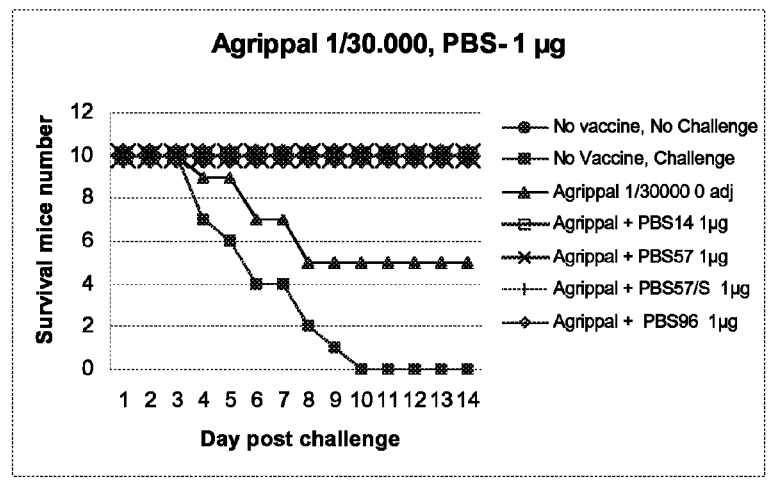
FIG. 12 shows survival of mice in a flu challenge model with a highly pathogenic H3N8 strain. Mice were vaccinated at day 0 with Agrippal® 1/30,000 and PBS-14, PBS-57 or PBS-96 liposomes, or PBS-57/S (PEGylated form) 1 μg (A), 100 ng (B) or 10 ng (C), and were challenged at day 21 with H3N8.
Figure 12:
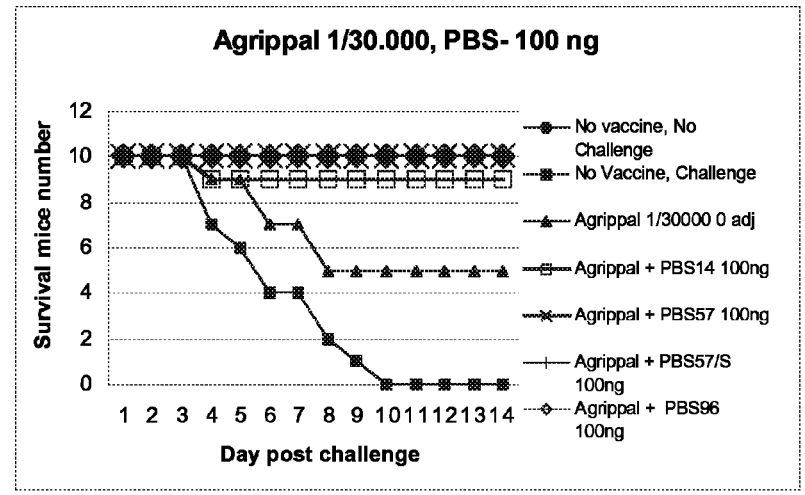
Figure 12:
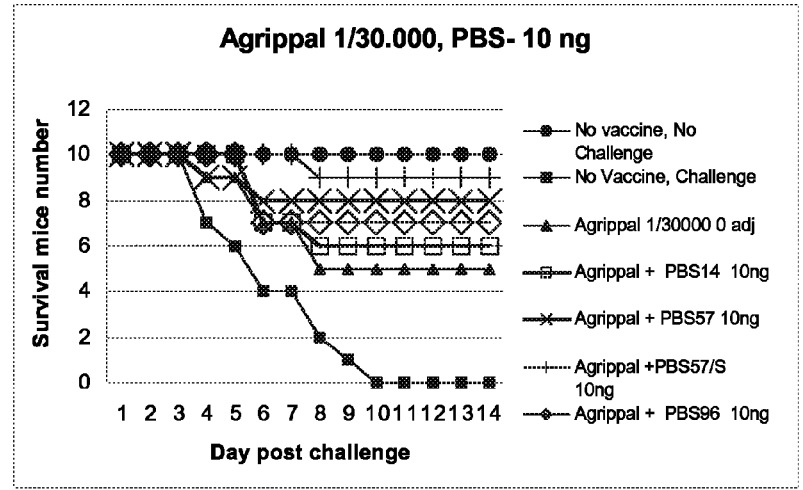

The results obtained with Fluarix® and Agrippal® are shown respectively on FIGS. 11 and 12. As demonstrated by the increased number of surviving mice, the adjuvants enhanced protection against challenge as compared with the Fluarix® or Agrippal® vaccine administered alone.

Example 8

In Vitro iNKT Activation

Adults PBMC and cord blood mononuclear cells (CBMC) were either non stimulated, or cultured in vitro with IL-2 alone or IL-2 combined with 100 ng α-GalCer or PBS-57/D or PBS-57/L (at 10 ng/ml or 100 ng/ml).

Figure 13:
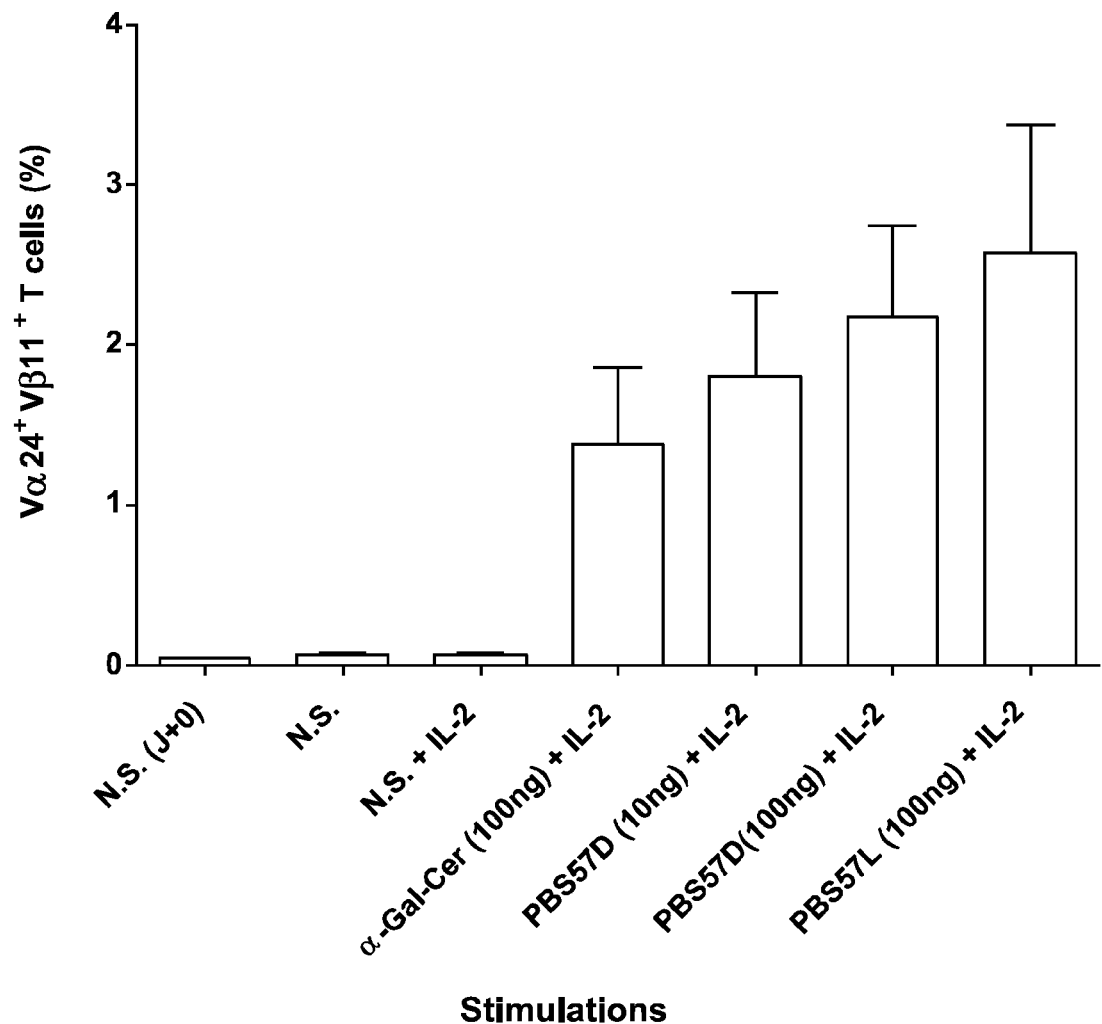
FIG. 13 shows the amplification of NKT cells after 7 days from adult PBMC (n=15).
Figure 14:
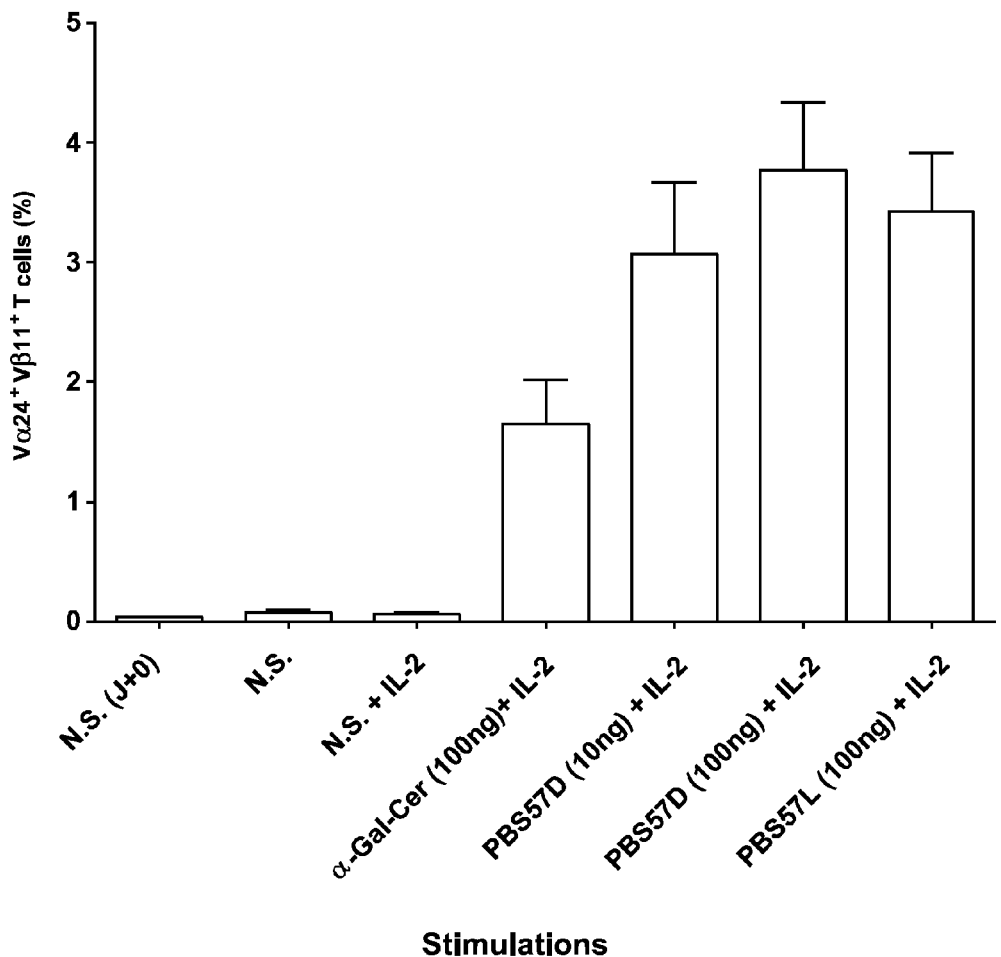
FIG. 14 shows the amplification of NKT cells after 7 days from cord blood mononuclear cells (CBMC) (n=20).

After 7 days of culture, activation of iNKT was determined by assessing the percentage of Vβ11/Vα24+ cells amplified from PBMC or CBMC (FIGS. 13 and 14).

The inventors demonstrated that PBS-57 induced a stronger activation of iNKT compared to α-GalCer, both in adults PBMC and CBMC.

Figure 15:
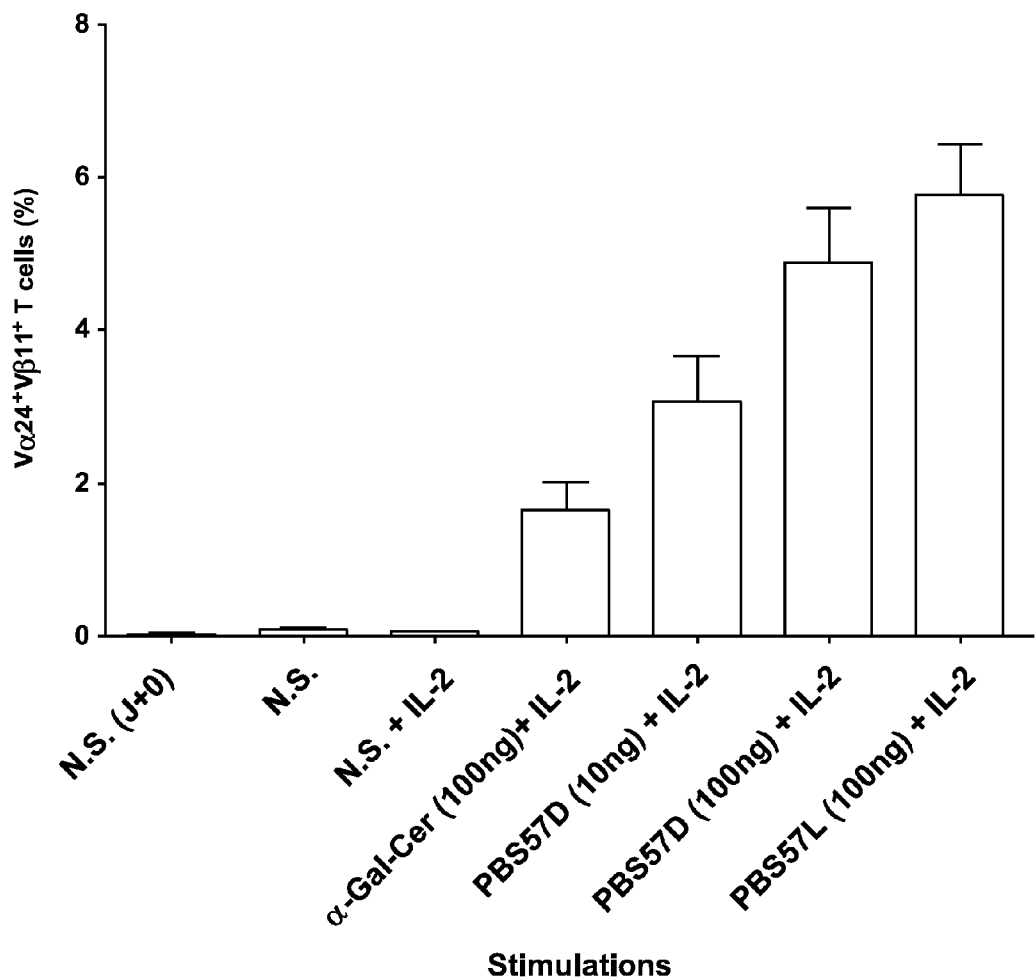
FIG. 15 shows the amplification of NKT cells after 7 days from elderly PBMC.

The same experiments are performed on elderly PBMC, i.e. PBMC from 65-years old or more adults. Similar results are obtainable (FIG. 15).

Example 9

ELISPOT on Monkey's PBMC Immunized with Adjuvants

Material and Methods

Animals

Young *Macaca fascicularis* of 3.5 kg from Mauritius were used with permission of the Noveprim Ethics Committee. Each macaque bears an individual identification number tattooed on the inner right thigh.

Immunization

Fluarix® alone or with 10 μg/kg or 100 μg/kg of PBS-57 or PBS-96 was injected twice in the same ipsilateral muscle area.

Sample Collection

Blood collection was performed 0, 21 or 42 days after immunization. PBMC were purified from the blood using a density gradient purification. They were then cultured and stimulated with Flu T cell epitopes or vaccine to evaluate IFN-γ responses in ELISPOT assays.

Results

Figure 16:
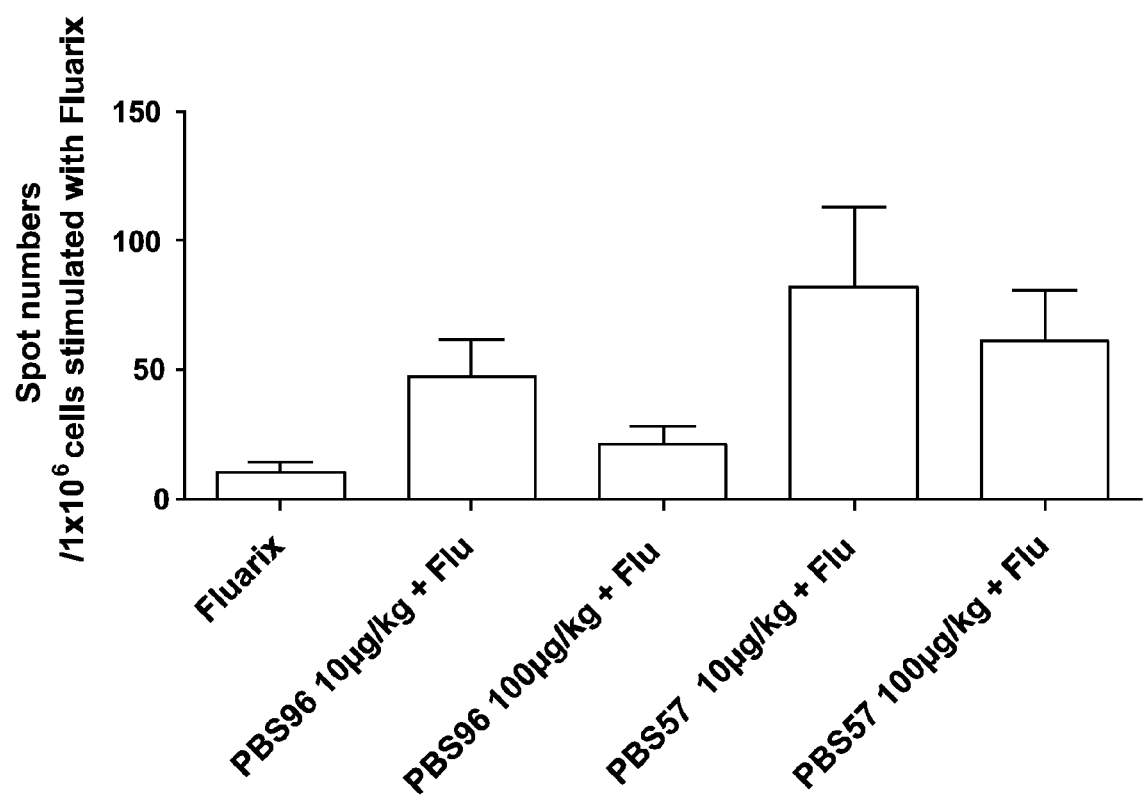
FIG. 16 shows the results of an ELISPOT assay performed on PBMCs of 60 monkeys immunized with Fluarix®, Fluarix®+PBS-96 or Fluarix®+PBS-57.

The inventors showed that an increased number of spots was obtained when the monkeys were immunized with Fluarix®+PBS-57 or Fluarix®+PBS-96 compared to Fluarix® alone (FIG. 16).

Example 10

H5N1 Challenge Study in Mice, Using Seasonal Fluarix® Vaccine with PBS-96

This study demonstrates the potency of PBS-96 to induce a cross-protection towards an influenza strain different from the one present in the tested vaccine.

Balb/c mice were used and immunized either with:

1) Nacl Mock (no infection)
2) Fluarix® alone (1/30,000)
3) PBS-96 (100 ng)
4) Fluarix®+PBS-96
5) NaCl T+

The mice were also injected intranasally with H5N1 virus (A/Vietnam 1194/04 strain) $10^4$ $CCID_{50}$. The number of living mice was determined each day.

The inventors showed that whereas mice immunized with Fluarix® were almost all dead 8 days after infection, 41% of the mice immunized with Fluarix®+PBS-96 were still alive 20 days after infection (FIG. 17).

Example 11

Detection of IgG1 and IgG2b in Mouse Sera After a Single Intramuscular Administration of Agrippal® Vaccine and N-acetylglycolipid Adjuvants Mice were injected at day 0 with:
PBS,
1 μg Agrippal® alone,
1 μg Agrippal®+1 μg PBS-57 in pegylated form or liposome formulation (PBS-57/S or PBS-57/L)
4 μg Agrippal® alone,
4 μg Agrippal®+1 μg PBS-57/S or PBS-57/L,
8.9 μg Agrippal® alone, or
8.9 μg Agrippal®+1 μg PBS-57/S or PBS-57/L.

Figure 18:
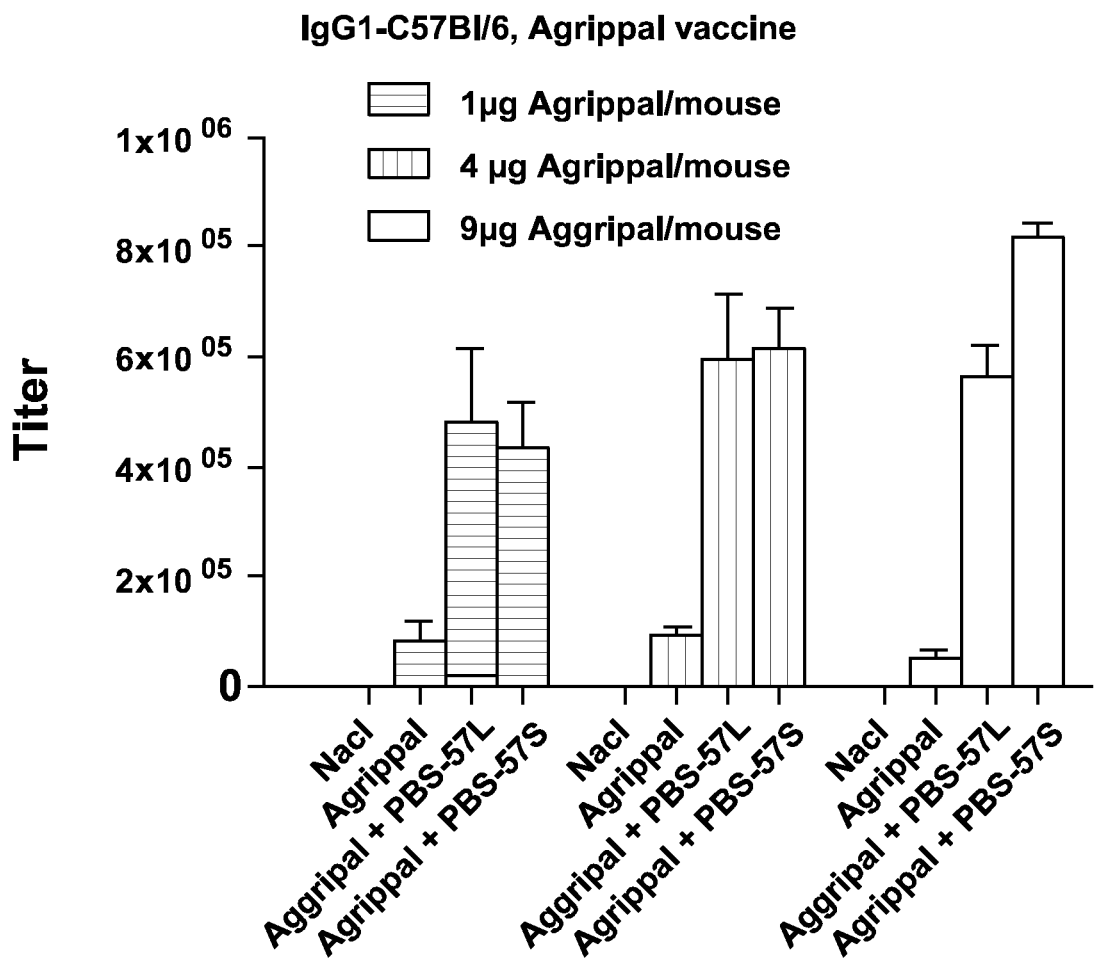
FIG. 18 shows the level of IgG1 detected in the sera of mice immunised once with PBS alone, Agrippal® vaccine alone, or Agrippal® vaccine combined with PBS-57 adjuvant (/S: PEGylated form; /L: liposome). The experiments were made with 1, 4 or 9 μg Aggripal® vaccine per mouse.
Figure 19:
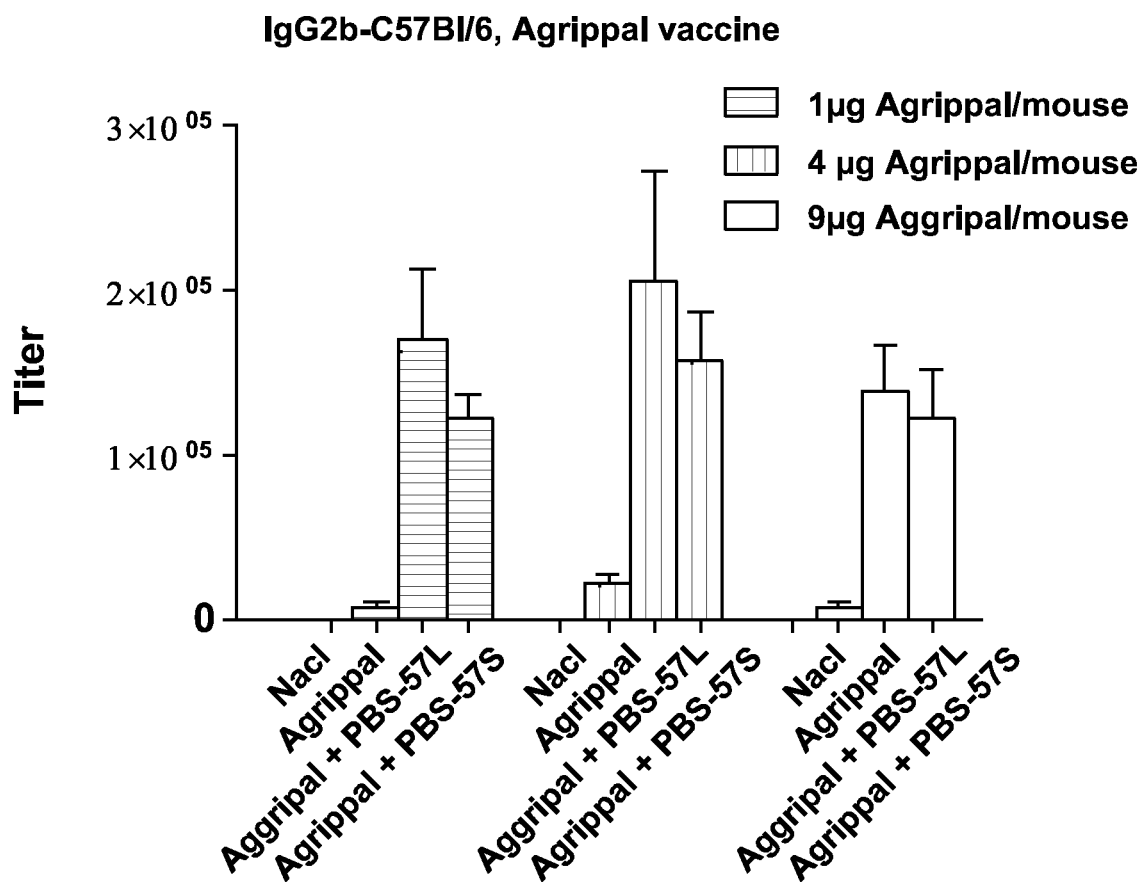
FIG. 19 shows the level of IgG2b detected in the sera of mice immunised once with PBS alone, Agrippal® vaccine alone, or Agrippal® vaccine combined with PBS-57 adjuvant (/S: PEGylated form; /L: liposome). The experiments were made with 1, 4 or 9 μg Aggripal® vaccine per mouse.

Sera were collected at day 21 and the IgG1 and IgG2b content of the sera was analysed by ELISA. Results are displayed on FIGS. 18 and 19. The analyses show that whereas increased levels of Agrippal®, when administered alone, do not enhance the level of IgG1 and IgG2b produced, the combination of Agrippal® with PBS-57, even with the lowest dose of Agrippal®, increases the amount of detectable IgG1 and IgG2b. Noteworthy, the levels of IgG1 and IgG2b were not significantly further increased when the dose of Agrippal® combined to PBS-57 was increased.

Similar results were obtained with PBS-14 and PBS-96.

Example 12

Indirect Hemagglutination Assay (IHA) Testing of Mice Sera Immunized Once with Agrippal®

Mice were injected by intramuscular route at day 0 with:
PBS,
1 μg PBS-57 in DMSO (PBS-57/D) alone
1 μg PBS-57 in PEGylated form (PBS-57/S) alone,
1 μg PBS-57 in liposome formulation (PBS-57/L) alone,
4 μg Agrippal® alone,
8.9 μg Agrippal® alone,
4 μg Agrippal®+1 μg PBS-57/D, PBS-57/S or PBS-57/L, or
8.9 μg Agrippal®+1 μg PBS-57/D, PBS-57/S or PBS-57/L.

Agrippal® vaccine comprises a mixture of A/Brisbane/10/2007-like, A/Brisbane/59/2007-like, and B/Florida/4/2006-like strains.

Figure 20:
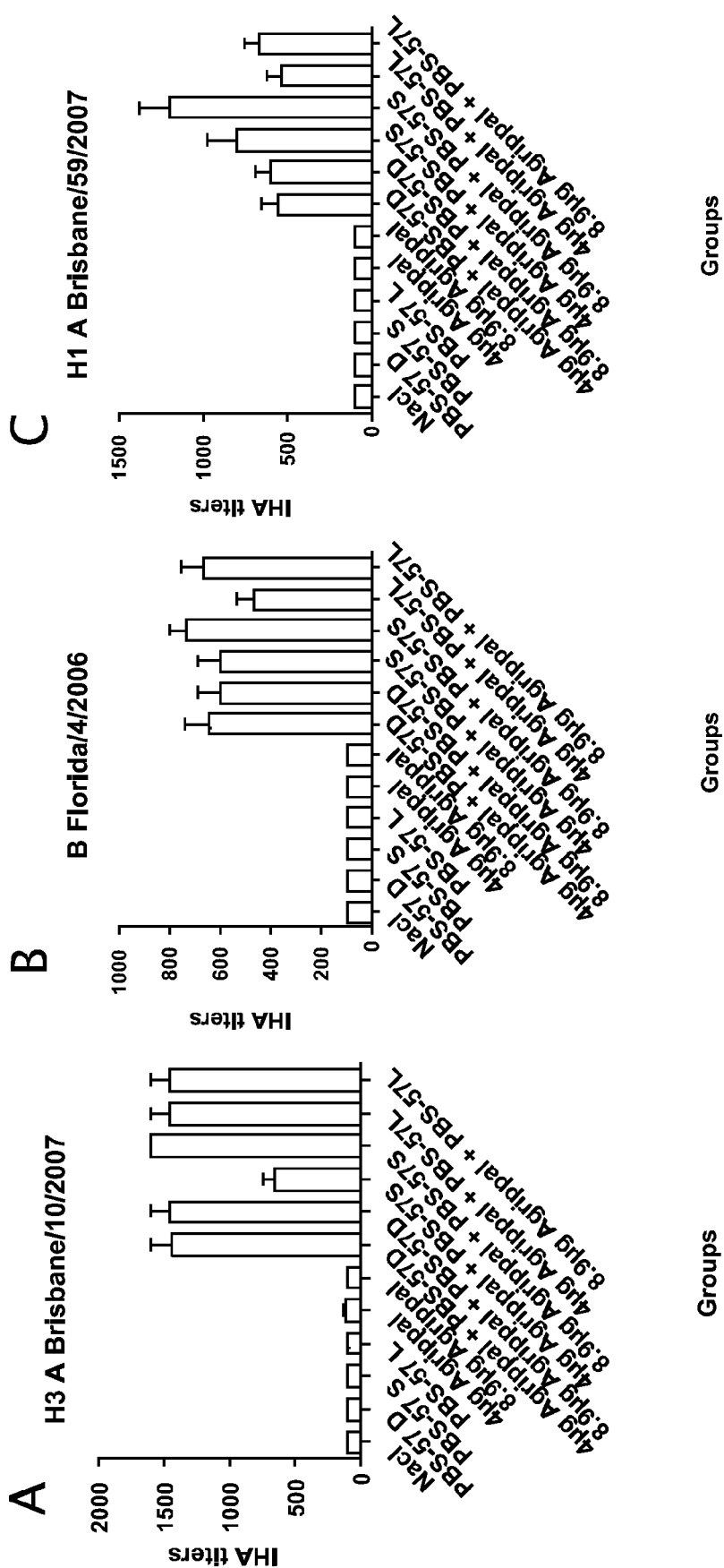
FIG. 20 shows IHA (indirect hemagglutination assay) titers measured in mice immunised once with 4 μg or 8.9 μg Agrippal® vaccine alone or combined with PBS-57/S, PBS-57/L or PBS-57/D (/S: PEGylated form; /L: liposome; /D: DMSO). A: IHA titer for strain A/Brisbane/10/2007; B: IHA titer for strain A/Brisbane/59/2007; C: IHA titer for strain B/Florida/4/2006.

Sera were collected at day 21 and reactivity with the three prototypical strains (H3 A/Brisbane/10/2007, H1 A/Brisbane/59/2007, and B/Florida/4/2006) of Agrippal® vaccine was assayed by measuring IHA titers for each of these strains (see FIG. 20).

It was found that PBS-57 increased IHA titers as compared with the Agrippal® vaccine alone.

The same results were obtained with PBS-96 and PBS-14, and with Fluarix® instead of Aggripal®.

The invention claimed is:

1. A method for treating or preventing influenza in an individual, the method comprising administering to the individual a prophylactically or therapeutically effective quantity of a vaccine composition, wherein the vaccine composition comprises:
   - at least one prophylactically active agent against influenza, and
   - at least one adjuvant, wherein the adjuvant is a derivative of a galactosylceramide,
   - wherein the at least one prophylactically active agent against influenza is selected from the group consisting of a live attenuated influenza virus, a killed or inactivated influenza virus, a subunit of an influenza virus, a recombinant polypeptide or protein from an influenza virus, a cDNA from an influenza virus or a recombinant influenza virus, of a first strain of influenza virus; wherein the vaccine composition is effective against a second strain of influenza virus different from the first strain of influenza virus, and wherein the vaccine composition is administered intramuscularly.

2. The method of claim 1, wherein the subunit of an influenza virus is an hemagglutinin.

3. The method of claim 1, wherein the first and second influenza viruses have a host, and wherein the host of the influenza virus is selected from the group consisting of a human, a horse and a bird.

4. The method of claim 1, wherein the first and second influenza viruses are selected from the group consisting of H1N1, H1N2, H2N2, H3N1, H3N2, H5N1, and H7N7 strains.

5. The method of claim 1, wherein the adjuvant is a compound having the following formula (V):

(V)

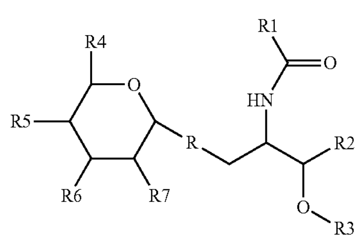

wherein:

R is an oxygen or a sulphur atom or $-CH_2-$;

$R_1$ is a saturated or unsaturated, optionally aromatic, linear or branched hydrocarbon chain such as an alkyl, aryl, aralkyl, alkenyl, or aralkenyl chain, comprising from 1 to 150 carbon atoms, optionally comprising one or more heteroatoms or groups preferably selected among O, N, S or a carbonyl group, and optionally substituted by one or more hydroxyl or cycloproppyl groups;

$R_2$ is a saturated or unsaturated, optionally aromatic, linear or branched hydrocarbon chain such as an alkyl, aryl, aralkyl, alkenyl or aralkenyl chain, comprising from 1 to 150 carbon atoms, optionally comprising one or more heteroatoms or groups preferably selected among O, N, S or a carbonyl group, and optionally substituted by one or more hydroxyl groups or by a saturated or unsaturated hydrocarbon chain comprising from 1 to 20 carbon atoms;

$R_3$ is an hydrogen atom or a saturated or unsaturated, optionally aromatic, linear or branched hydrocarbon chain such as an alkyl, aryl, aralkyl, alkenyl or aralkenyl chain, comprising from 1 to 120 carbon atoms;

$R_4$, $R_5$, $R_6$ and $R_7$, identical or different, represent:

(i) an hydroxyl group or (ii) a saturated or unsaturated, optionally aromatic, linear or branched hydrocarbon chain such as an alkyl, aryl, aralkyl, alkenyl or aralkenyl chain, comprising from 1 to 100 carbon atoms, optionally comprising one or more heteroatoms or groups preferably selected among O, N, S or a carbonyl group; or (iii) an amino, sulphate, phosphate or carboxyl group, or (iv) a chain of 1 to 4 hexoses, optionally substituted by one or more groups selected from an amino, a sulphate, a phosphate and a carboxyl group, the hexoses being linked one to the other by an oxygen or a sulphur atom or $-CH_2-$.

6. The method of claim 1, wherein the adjuvant is a compound having the following formula (I)

(I)

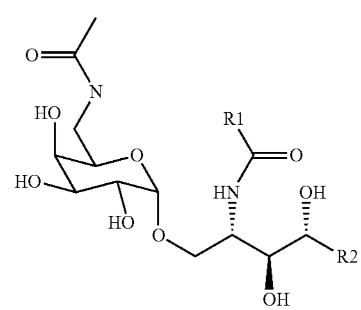

wherein $R_1$ is a) $-(CH_2)_XCH_3$ where X is an integer selected from 1 to 100; or b) $-(CH_2)_XCH{=}CH(CH_2)_YCH_3$ or $-(CH_2)_XCH{=}CH(CH_2)_YCH{=}CH(CH_2)_ZCH_3$ wherein X, Y, and Z are integers independently selected from 1 to 14; and $R_2$ is a linear or branched $C_3$-$C_{100}$ alkyl.

7. The method of claim 1, wherein the adjuvant is the compound PBS-57 of following formula (II)

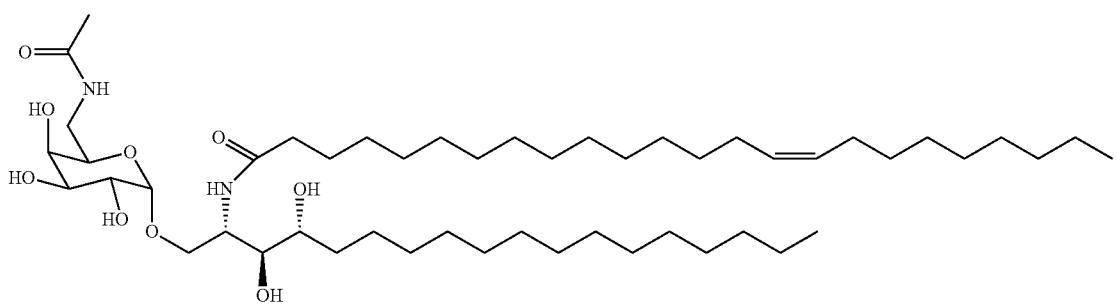
(II)
8. The method of claim 1, wherein the adjuvant is the compound PBS-96 of following formula (III)
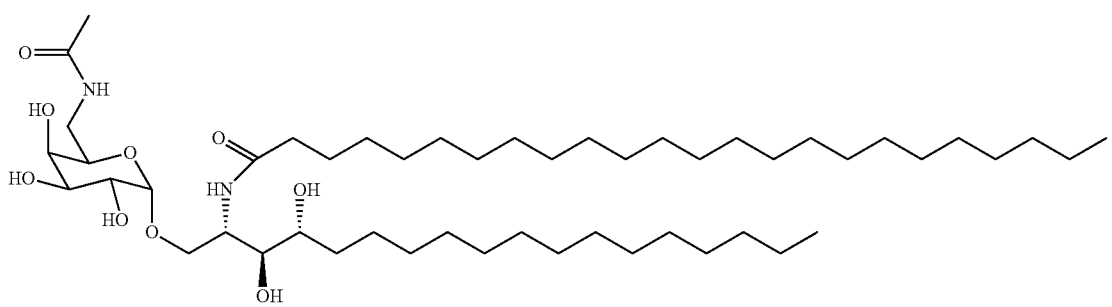
(III)
9. The method of claim 1, wherein the adjuvant is the compound PBS-14 of following formula (IV)
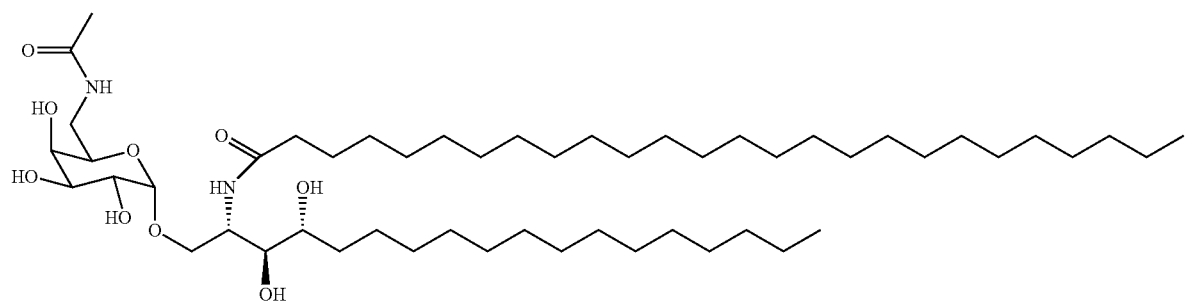
(IV)
10. The method of claim 1, wherein the vaccine composition comprises an additional adjuvant.
\* \* \* \* \*

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: H-2Kb NP

<400> SEQUENCE: 1
```

-continued

```
Ala Ser Asn Glu Asn Met Glu Thr Met
1               5
```